(12) United States Patent
Edens et al.

(10) Patent No.: US 7,985,375 B2
(45) Date of Patent: Jul. 26, 2011

(54) SAMPLE PREPARATION SYSTEM AND METHOD FOR PROCESSING CLINICAL SPECIMENS

(75) Inventors: Ted Carl Edens, Highland, MD (US); Richard Obiso, Christiansburg, VA (US); Gerard J. Sevigny, Nashua, NH (US); Michael Touma, Pelham, NH (US); Mark Messina, Manchester, NH (US); Brian McKeen, Bow, NH (US); Robert C. Aviles, Merrimack, NH (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 450 days.

(21) Appl. No.: 12/062,950

(22) Filed: Apr. 4, 2008

(65) Prior Publication Data

US 2008/0247914 A1 Oct. 9, 2008

Related U.S. Application Data

(60) Provisional application No. 60/910,565, filed on Apr. 6, 2007.

(51) Int. Cl.
*G01N 21/00* (2006.01)
(52) U.S. Cl. .......... 422/64; 422/50; 422/63; 422/65; 422/500; 422/511; 436/180
(58) Field of Classification Search .......... 422/63–65, 422/99–100, 50, 500, 511; 436/180
See application file for complete search history.

(56) References Cited

U.S. PATENT DOCUMENTS

| | | | |
|---|---|---|---|
| 4,151,950 A | 5/1979 | Gunnewig |
| 4,283,950 A | 8/1981 | Tervamäki |
| 4,478,095 A | 10/1984 | Bradley et al. |
| 4,696,144 A | 9/1987 | Bankuty et al. |
| 4,794,085 A | 12/1988 | Jessop et al. |
| 4,855,110 A | 8/1989 | Marker et al. |
| 4,970,053 A | 11/1990 | Fechtner |
| 5,063,790 A | 11/1991 | Freeman et al. |
| 5,075,082 A | 12/1991 | Fechtner |
| 5,174,762 A | 12/1992 | Hoppal et al. |
| 5,203,236 A | 4/1993 | Anderson |
| 5,313,858 A | 5/1994 | Stitt |
| 5,340,544 A | 8/1994 | Nishikawa et al. |
| 5,341,854 A | 8/1994 | Zezulka et al. |

(Continued)

FOREIGN PATENT DOCUMENTS

JP 2184762 7/1990

(Continued)

OTHER PUBLICATIONS

Written Opinion of the International Searching Authority for corresponding PCT Application No. PCT/US07/66177, date of completion Sep. 12, 2007.

(Continued)

*Primary Examiner* — Jyoti Nagpaul
(74) *Attorney, Agent, or Firm* — Hunton & Williams

(57) ABSTRACT

A system and method for automated handling of vials containing liquid medical specimens is disclosed. The robotic system processes the specimens for further downstream molecular analysis. The processing comprises automated vial cap removal, pipetting of the vial contents, transfer of the vial contents to a destination tray such as a multiwell plate, and recapping of the vial.

60 Claims, 8 Drawing Sheets

U.S. PATENT DOCUMENTS

| | | |
|---|---|---|
| 5,366,896 A | 11/1994 | Margrey et al. |
| 5,374,395 A | 12/1994 | Robinson et al. |
| 5,437,838 A | 8/1995 | DeMoranville et al. |
| 5,463,895 A | 11/1995 | Brentz |
| 5,481,946 A | 1/1996 | Nishikawa et al. |
| 5,490,321 A | 2/1996 | Kaneko |
| 5,499,545 A | 3/1996 | Kimura et al. |
| 5,503,036 A | 4/1996 | Nguyen et al. |
| 5,537,880 A | 7/1996 | Takeda et al. |
| 5,540,081 A | 7/1996 | Takeda et al. |
| 5,540,890 A | 7/1996 | Clark et al. |
| 5,550,059 A | 8/1996 | Boger et al. |
| 5,578,494 A | 11/1996 | Clark et al. |
| 5,604,101 A | 2/1997 | Hanley et al. |
| 5,627,522 A | 5/1997 | Walker et al. |
| 5,637,275 A | 6/1997 | Carey et al. |
| 5,652,568 A | 7/1997 | Ko |
| 5,675,715 A | 10/1997 | Bernstein et al. |
| 5,723,289 A | 3/1998 | Eaton et al. |
| 5,736,102 A | 4/1998 | Seaton et al. |
| 5,737,498 A | 4/1998 | Murray |
| 5,753,186 A | 5/1998 | Hanley et al. |
| 5,778,740 A | 7/1998 | Tye |
| 5,814,276 A | 9/1998 | Riggs |
| 5,819,508 A | 10/1998 | Kraft et al. |
| 5,861,563 A | 1/1999 | Boyd et al. |
| 5,876,670 A | 3/1999 | Mitsumaki et al. |
| 5,897,835 A | 4/1999 | Seaton et al. |
| 5,915,282 A | 6/1999 | Merriam et al. |
| 5,919,706 A | 7/1999 | Tajima |
| 5,965,828 A | 10/1999 | Merriam |
| 5,966,309 A | 10/1999 | O'Bryan et al. |
| 5,985,672 A | 11/1999 | Kegelman et al. |
| 5,988,857 A | 11/1999 | Ozawa et al. |
| 6,022,747 A | 2/2000 | Gherson et al. |
| 6,060,022 A | 5/2000 | Pang et al. |
| 6,060,320 A | 5/2000 | Dorenkott et al. |
| 6,065,617 A | 5/2000 | Cohen et al. |
| 6,076,330 A | 6/2000 | Thomas et al. |
| 6,100,094 A | 8/2000 | Tajima |
| 6,105,343 A | 8/2000 | Grove et al. |
| 6,117,398 A | 9/2000 | Bienhaus et al. |
| 6,121,049 A | 9/2000 | Dorenkott et al. |
| 6,123,205 A | 9/2000 | Dumitrescu et al. |
| 6,126,903 A | 10/2000 | Preston et al. |
| 6,142,039 A | 11/2000 | Herring, Sr. |
| 6,156,575 A | 12/2000 | Fassbind et al. |
| 6,170,232 B1 | 1/2001 | VandeGeijn |
| 6,202,278 B1 | 3/2001 | Nakayama et al. |
| 6,216,340 B1 | 4/2001 | Fassbind et al. |
| 6,257,091 B1 | 7/2001 | Cohen et al. |
| 6,293,750 B1 | 9/2001 | Cohen et al. |
| 6,326,147 B1 | 12/2001 | Oldham et al. |
| 6,331,437 B1 | 12/2001 | Cohen et al. |
| 6,332,636 B1 | 12/2001 | Cohen et al. |
| 6,335,166 B1 | 1/2002 | Ammann et al. |
| 6,347,552 B1 | 2/2002 | Purpura et al. |
| 6,358,474 B1 | 3/2002 | Dobler et al. |
| 6,370,942 B1 | 4/2002 | Dunfee et al. |
| 6,415,669 B1 | 7/2002 | Carl |
| 6,417,008 B2 | 7/2002 | Tyberg et al. |
| 6,436,349 B1 | 8/2002 | Carey et al. |
| 6,484,556 B1 | 11/2002 | Jabobs et al. |
| 6,498,037 B1 | 12/2002 | Carey et al. |
| 6,499,364 B1 | 12/2002 | Suovaniemi |
| 6,553,824 B1 | 4/2003 | Lutze |
| 6,562,299 B1 | 5/2003 | Ostgaard et al. |
| 6,562,568 B1 | 5/2003 | Kleiber et al. |
| 6,572,824 B1 | 6/2003 | Ostgaard et al. |
| 6,573,088 B2 | 6/2003 | Gemmell et al. |
| 6,576,477 B1 | 6/2003 | Tokiwa et al. |
| 6,581,647 B1 | 6/2003 | Leidlein et al. |
| 6,604,337 B2 | 8/2003 | Close et al. |
| 6,604,903 B2 | 8/2003 | Osborne et al. |
| 6,605,213 B1 | 8/2003 | Ammann et al. |
| 6,622,578 B2 | 9/2003 | Carl |
| 6,689,318 B1 | 2/2004 | Spork et al. |
| 6,723,289 B2 | 4/2004 | Iheme et al. |
| 6,734,424 B2 | 5/2004 | Lennon et al. |
| 6,764,649 B2 | 7/2004 | Ammann |
| 6,773,927 B2 | 8/2004 | Osawa et al. |
| 6,810,757 B2 | 11/2004 | Carl |
| 6,852,283 B2 | 2/2005 | Acosta et al. |
| 6,871,566 B2 | 3/2005 | Niwayama et al. |
| 6,890,742 B2 | 5/2005 | Ammann et al. |
| 6,919,175 B1 | 7/2005 | Bienhaus et al. |
| 6,938,504 B2 | 9/2005 | Camenisch |
| 6,943,181 B2 | 9/2005 | Sundermann et al. |
| 6,956,055 B2 | 10/2005 | Sundermann et al. |
| 6,959,952 B2 | 11/2005 | Williams |
| 6,978,689 B2 | 12/2005 | Carl |
| 6,984,527 B2 | 1/2006 | Miller |
| 7,087,607 B2 | 8/2006 | Gerlach et al. |
| 7,150,190 B2 | 12/2006 | Krufka et al. |
| 7,152,504 B2 | 12/2006 | Itoh |
| 7,233,838 B2 | 6/2007 | Barry et al. |
| 7,251,921 B2 | 8/2007 | Galimberti et al. |
| 7,282,182 B2 | 10/2007 | Dale et al. |
| 7,284,900 B2 | 10/2007 | Mayer |
| 7,322,170 B2 | 1/2008 | Tomalesky et al. |
| 7,377,027 B2 | 5/2008 | Mayer |
| 7,409,809 B1 | 8/2008 | Degen et al. |
| 7,416,706 B2 | 8/2008 | Brunner et al. |
| 7,421,831 B2 | 9/2008 | Neeper et al. |
| 7,477,997 B2 | 1/2009 | Kaplit |
| 7,501,094 B2 | 3/2009 | Bysouth et al. |
| 7,537,735 B2 | 5/2009 | Hiemer et al. |
| 7,556,777 B2 | 7/2009 | Victor |
| 7,572,638 B2 | 8/2009 | Pressman et al. |
| 7,575,937 B2 | 8/2009 | Wiggli et al. |
| 7,581,660 B2 | 9/2009 | Nay et al. |
| 7,634,378 B2 | 12/2009 | Kaplit |
| 7,635,246 B2 | 12/2009 | Neeper et al. |
| 7,681,466 B2 | 3/2010 | Miller et al. |
| 7,694,591 B2 | 4/2010 | Leibfried |
| 7,783,383 B2 | 8/2010 | Eliuk et al. |
| 7,792,647 B1 | 9/2010 | Ding et al. |
| 2003/0092186 A1 * | 5/2003 | Pressman et al. .......... 436/46 |
| 2005/0158212 A1 | 7/2005 | Yavilevich |
| 2006/0115889 A1 | 6/2006 | Nakashima et al. |
| 2007/0006550 A1 | 1/2007 | Kemper et al. |
| 2007/0020764 A1 | 1/2007 | Miller |
| 2008/0019878 A1 | 1/2008 | Trump |
| 2008/0022808 A1 | 1/2008 | Owen et al. |
| 2008/0038827 A1 | 2/2008 | Miller et al. |
| 2008/0090288 A1 | 4/2008 | Hibino et al. |
| 2008/0160599 A1 | 7/2008 | Weber-Matthiesen et al. |
| 2008/0170967 A1 | 7/2008 | Itoh |
| 2008/0247914 A1 | 10/2008 | Edens et al. |
| 2009/0003981 A1 | 1/2009 | Miller |
| 2009/0028754 A1 | 1/2009 | Robb |
| 2009/0117620 A1 | 5/2009 | Fritchie et al. |
| 2009/0266149 A1 | 10/2009 | Kaplit |
| 2009/0318276 A1 | 12/2009 | Miller |
| 2010/0015007 A1 | 1/2010 | Pedrazzini |
| 2010/0215548 A1 | 8/2010 | De Luca et al. |
| 2010/0241270 A1 | 9/2010 | Eliuk et al. |

FOREIGN PATENT DOCUMENTS

| | | |
|---|---|---|
| WO | WO 2006/054964 | 5/2006 |
| WO | WO 2006/081612 | 8/2006 |
| WO | WO 2008/123882 | 10/2008 |
| WO | WO 2009/068555 | 6/2009 |
| WO | WO 2010/038852 | 4/2010 |
| WO | WO 2010/057861 | 5/2010 |

OTHER PUBLICATIONS

International Search Report for corrresponding PCT Application No. PCT/US07/66177 date of completion Sep. 4, 2007, mailed Sep. 25, 2007.

* cited by examiner

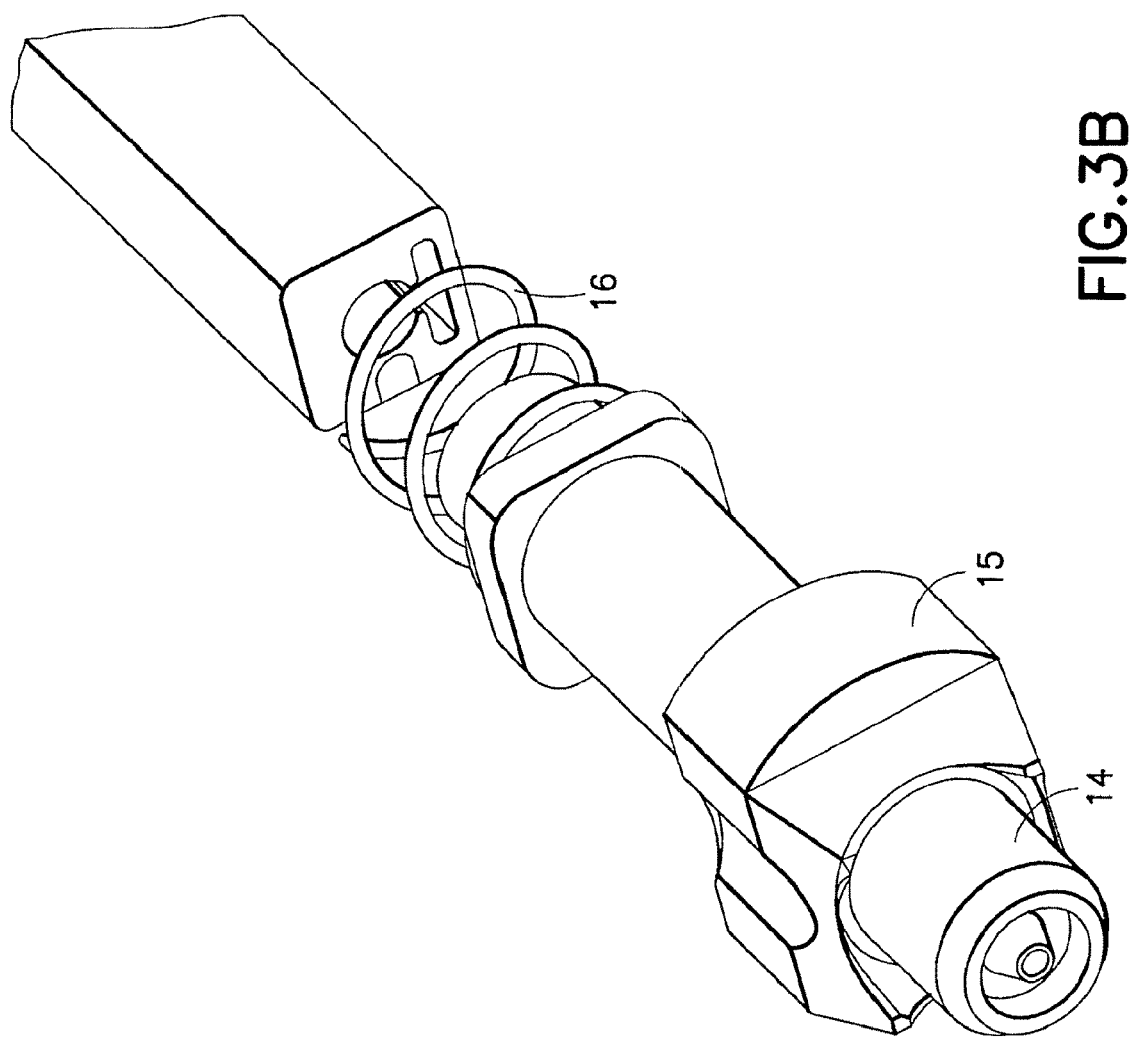

SAMPLE PREPARATION SYSTEM AND METHOD FOR PROCESSING CLINICAL SPECIMENS

This patent application claims the benefit of U.S. provisional patent application Ser. No. 60/910,565, filed on Apr. 6, 2007.

FIELD OF THE INVENTION

The sample preparation system and method relates to the processing of clinical samples or specimens. In certain aspects, the system and method relates to the automated transfer of samples or specimens from an initial container or receptacle to a destination container or receptacle. In other aspects, the system and method relates to transfer of samples or specimens to a destination container or receptacle for further processing, to perform an assay, or to perform other analysis. In other aspects, the system and method relates to transfer of portions of samples or specimens to a destination container or receptacle and the preservation of the remaining samples or specimens for further processing, assays, analysis, archiving, or other uses or purposes.

BACKGROUND

With increasing need for medical diagnostics, increasingly large volumes of clinical samples are being processed. Processing of clinical samples and specimens can involve, among other things, the transfer of samples or specimens to containers or receptacles suitable for the diagnostic testing to be performed. Processing of samples and specimens can include steps of accessing the contents of an initial container or receptacle, for example by removing the cover, removing a portion of the contents, and transferring a portion of the contents to a destination container or receptacle. In some situations, processing can include replacing the cover of or otherwise closing the initial container or receptacle to preserve the remaining contents for further testing or archiving.

The processing of large numbers of samples and specimens increases the time in providing results of the diagnostics, increases the exposure of workers to repetitive motion disorders and to potentially bioharzardous materials, reduces consistency of sample or specimen preparation, and increases the cost of the diagnostic procedure. As the volume of medical diagnostic testing increases, the number of samples and specimens that require processing increases. Automation of the sample preparation process for medical diagnostic testing addresses the issues identified above by reducing the time required to process specimens, reducing the exposure of workers to repetitive motion and biohazardous materials, providing for consistency in the processing of samples, and helping to contain the cost of processing specimens.

BRIEF SUMMARY

In one aspect, the present system is an instrument for the automated handling of medical samples for molecular analysis. The instrument uses several mechanical arms and devices to manipulate vials or other containers or receptacles containing medical or clinical specimen or sample material. In another aspect, the present system provides a method of automatically processing medical or clinical specimens or samples for molecular or other diagnostic analysis. In an illustrative embodiment, the present system autonomously processes cytological samples and specimens for molecular analysis. Autonomous processing of samples and specimens may include accessing the contents of an initial container or receptacle, for example by removing a cap or cover, removing all or a portion of the contents, transferring all or a portion of the contents to a destination container or receptacle, and, in some embodiments, replacing the cover of or otherwise closing the initial container or receptacle to preserve the remaining contents for further testing or archiving.

In one aspect, a sample preparation system (SPS) is a microprocessor-controlled robotic device that automates the processing of clinical specimens contained in vials or other containers to destination receptacles for further processing and assay analysis. The SPS is able to automatically process large numbers of sample- or specimen-containing vials and other containers. The microprocessor-control may be implemented with any logic or processor including, ASIC's, specialized logic or other integrated circuits. The automated control may be implemented with any logic or processor including, ASIC's, specialized logic or other integrated circuits or any other combination of electrical-mechanical or mechanical control devices.

The manual removal of caps from a vial or other container to transfer a sample to a destination receptacle and then recapping the vial presents concerns for workers who would be required to perform this repetitive task for large numbers of vials or other containers. For example, manual uncapping and recapping of medical or clinical samples and specimens presents the potential for exposure to biohazardous materials, repetitive motion injuries, fatigue, and reduced efficiency. Embodiments of the SPS are more adept at performing this repetitive task and reducing overall test turnaround time, and also in reducing exposure of workers to potential repetitive motion disorders and biohazardous materials.

DETAILED DESCRIPTION

Figure 1:
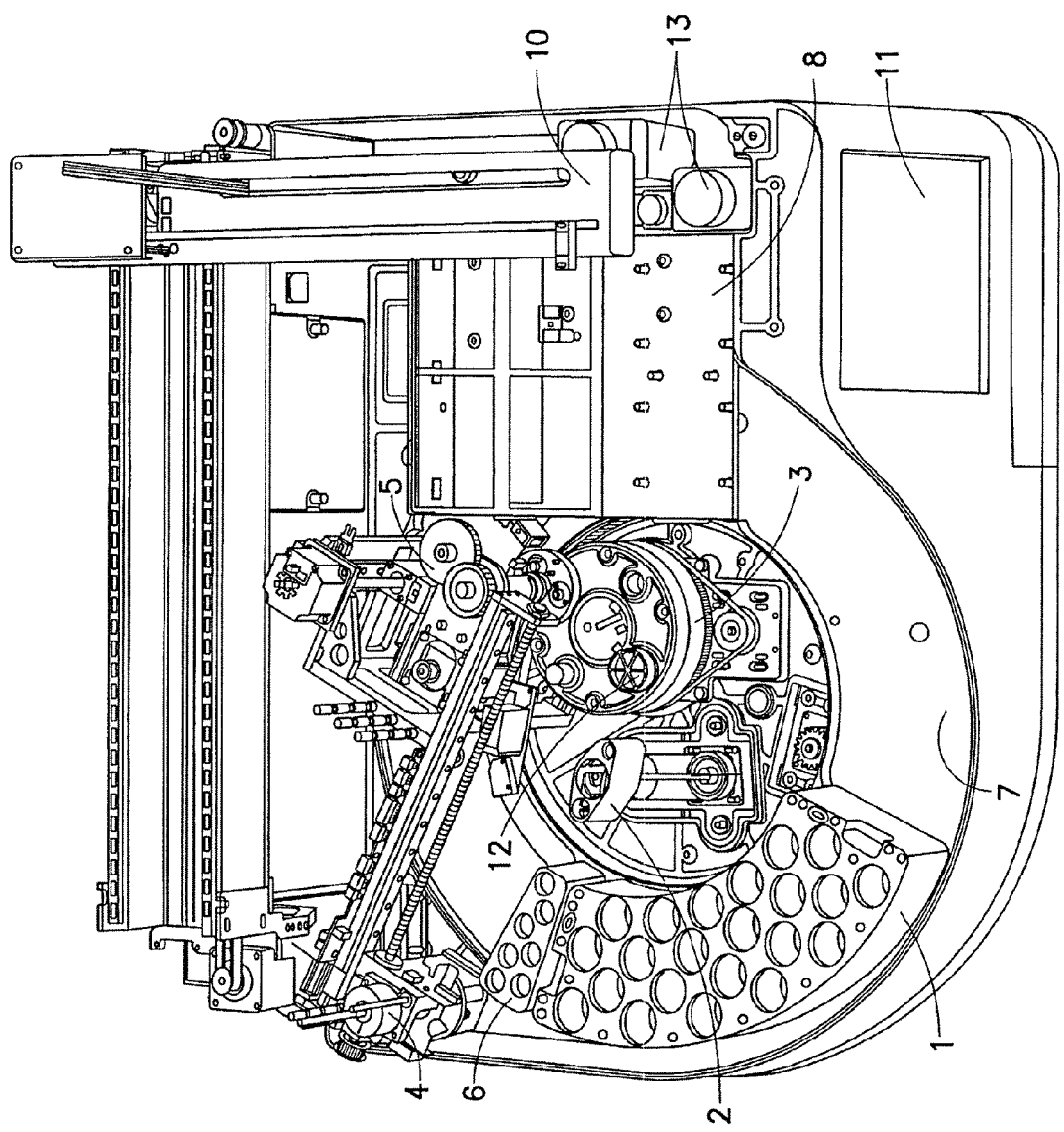
FIG. 1. Top view of the sample preparation system.

In one illustrative embodiment, the SPS processes samples for a molecular diagnostic assay by decapping a vial, allowing access to the contents of the vial, pipetting a volume of sample from the vial, and recapping the vial. Another further embodiment of the SPS includes pipetting a predetermined or specified volume of sample before the vial is recapped. A vial may contain a liquid sample, a control for a molecular diagnostic assay, a specimen to be tested in a molecular diagnostic assay, or a liquid-based cytology medium containing a specimen. The liquid-based cytology medium or sample medium can be a medium that is compatible with molecular analysis or a medium that preserves and assists in the transport of specimens for further molecular or diagnostic analysis or for archiving. Archived samples may be stored and further tested. The SPS can use specimen samples that have been previously sampled for other assays. Recapping of specimen samples by the SPS after specimen processing allows further storage and sampling of specimens.

The illustrative SPS processes a plurality of capped vials by agitating each vial to mix the vial contents or resuspend certain vial contents, decapping the vial, pipetting out an aliquot of the contents, and transferring this sample into a destination receptacle for further processing. In another illustrative embodiment, the SPS processes a capped vial by decapping the vial, pipetting out an aliquot of the contents, recapping the vial, and transferring the contents into a destination receptacle for further processing. In yet another illustrative embodiment, the SPS processes a capped vial by agitating the vial to mix the vial contents or resuspend certain vial contents, decapping the vial, pipetting out an aliquot of the contents, recapping the vial, and transferring the contents into a destination receptacle for further processing. In other illustrative embodiments, the SPS processes a plurality of capped vials by chemically mixing or resuspending some or all of the vial contents before decapping the vial to pipetting out an aliquot of the contents or by separating components of the vial chemically (e.g., precipitation), physically (e.g., centrifugation) or otherwise before decapping the vial to pipetting out an aliquot of the contents. In yet other illustrative embodiments, the SPS processes a plurality of capped vials by chemically (e.g., chemical denaturation), physically (e.g., heat denaturation) or otherwise treating or transforming the vial contents before decapping the vial to pipetting out an aliquot of the contents.

The destination area or receptacle may include any support or containment area including but not limited to filter paper, slides, a multiwell plate, a multiwell filtration unit wherein liquid medium may be removed while sample material is retained, an array of tubes, a rack of tubes, an array of filtration units, a rack of filtration units, thermocycler plates, thermocycler tubes, microarray, biochip, or any combination of the above. Any support or containment area that can handle an aliquot of sample from a vial or container processed by the SPS is a suitable destination area or receptacle.

Any specimen or sample vial 12 or other container may be used in the sample preparation system. Any specimen vial cap may also be used in the sample preparation system. Suitable caps include screw caps, plug caps, or any cap that may be removed by the action of a capper arm 5. A specimen vial may include any vial or container that is capable of being handled by the SPS. A specimen vial may contain samples, blanks, controls, washes or any fluid or compound that the SPS can process.

In an illustrative embodiment, the medium used for collecting or transporting medical specimens may be any liquid medium that is able to preserve a biological specimen for molecular analysis at a later time. More preferable for the medium is a liquid-based cytology medium. More preferably this liquid medium may be used for both cytological and molecular analysis of the specimen. More preferable is a medium that may be used for preserving and transporting a biological specimen. Still more preferable is a medium that is suitable for preserving and transporting a specimen wherein the specimen will undergo molecular analysis for microorganisms. Yet still more preferable is a medium where the specimen will undergo molecular analysis for UPV, Chlamydia, Cytomegalovirus, HIV, Treponema, and/or Neisseria.

In an illustrative embodiment, the SPS comprises a staging carousel for vials or other containers during decapping and recapping and the pipetting of vial or container contents. This staging carousel preferably comprises one or more vial or container wells of one or more sizes for vial and other container holding and gripping.

In an illustrative embodiment, a method of processing samples comprises transferring vials to a staging carousel so that a vial can be uncapped, an aliquot removed, and recapped. In a further illustrative embodiment, the method further comprises holding the cap while an aliquot is being removed. In yet a further illustrative embodiment, the aliquot that is removed is of a predetermined amount.

Decapping may be accomplished by a device that removes the cap while another device holds the vial sufficiently stationary to allow for decapping. For screw or twist-off caps, a decapping device grasps a vial cap and rotates the vial cap so that the vial cap unscrews or untwists from the vial. During decapping, the vial may be held or rendered stationary by a vial gripping device or by a passive device whereby the vial is held or rendered stationary by the fit of a specially designed vial and/or corresponding or mating vial holder. Similarly, a screw or twist-off cap may be removed from a vial based upon a cap gripping device or a corresponding or mating vial cap holder, allowing rotation of the cap. The decapping device also allows the holding of a cap during sample removal and the recapping of vials afterward.

Vial gripping may be accomplished by a device that grasps a vial to hold it or render it sufficiently stationary to allow vial cap removal. In one embodiment, a vial gripping device grasps a vial during decapping and has the ability to loosen that grasp so that after recapping, the vial can be moved. An illustrative sample preparation system incorporates a vial gripping device that can hold or render stationary any vial, thereby eliminating the need for a specially designed vial.

In an illustrative embodiment, pipetting is used by the SPS to transfer a sample from a vial to a destination receptacle. The amount of sample that is pipetted may be predetermined by the operator, may be based upon the size of the vial, or based upon the level of liquid in the vial as determined by a liquid level sensor. In all instances, a desired amount of liquid is withdrawn by the specimen transfer pipette assembly from an uncapped vial and transferred to the destination receptacle.

Destination areas or receptacles may include but are not limited to filter paper, slides, microarrays, biochips, deep well filtration plates and multi-well microplates such as 96-deep well filtration plates, 96-well microplates, 384-well filtration plates, and 384-well microplates. Destination receptacles also include a rack of tubes or an array of tubes. A destination receptacle may be any suitable container that can accept and hold an aliquot of a liquid specimen. Destination areas or receptacles may be located in a holding area 8.

In an illustrative embodiment of the SPS, samples loaded onto the SPS have been previously sampled for analysis. Depending upon the prior sampling, the amount of sample in each container may vary from container to container. Therefore, the quantity of specimen remaining in the sample vial may be insufficient for further testing and must be determined. Prior to sampling, the SPS measures the amount of sample remaining in the container. The amount of sample may then be determined for sufficiency in performing a downstream assay. Additionally, recapping of sample vials by the SPS after sample removal allows storage, archiving and further testing of the sample.

Assemblies of an Illustrative Sample Preparation System

An exemplary embodiment of the sample preparation system may include one or more of the following subassemblies: Input Platform Holding Racks 1, Input Platform 7, Mixing Basket 2, Vial Handling Arm 4, Staging Platform 3, Capper Arm 5, Tip Head Assembly with Detector 9, Bar code Reader, Computer Control.

Input Platform

The input platform supports and moves several removable input racks. In one embodiment, the input platform is a carousel and the input racks comprise the semi-circular segments of the illustrative input carousel. These racks are set upon an input carousel connected to a drive mechanism, allowing rotation of the input carousel and the input carousel racks. Rotation of the input carousel moves samples contained in the input carousel racks so they are accessible to the robotic vial handler arm 4. The input carousel racks have a plurality of circular wells sized for holding vials. Each of these input carousel racks is removable from the input carousel mechanism of the SPS, where normally they rest on top of the rotatable carousel base. The removable input carousel racks allow loading of the rack outside the SPS, holding and organizing vials, and storing vials after runs. Each input carousel rack comprises a semi-circular segment of the whole input carousel where a complete input carousel is formed when each of the input carousel racks are placed in the SPS. A smaller vial rack 6 with a plurality of circular wells for holding vials containing control solutions and comprising a smaller segment of the input carousel completes the input carousel of the SPS.

In alternate embodiments, one or more input platform or vial racks may have wells of different shapes, sizes, and dimensions to accommodate various shapes, sizes, and dimensions of specimen vials in a run or workflow of the SPS.

In yet other embodiments, the input platform and input platform racks are not circular and may be any shape and may move in any fashion as long as the vials are accessible to the various components of the SPS. Additionally, in other embodiments, the input platform and input platform racks may be stationary, with access to the vials using the robotic arms of the SPS.

Vial Handler Arm

Figure 2:
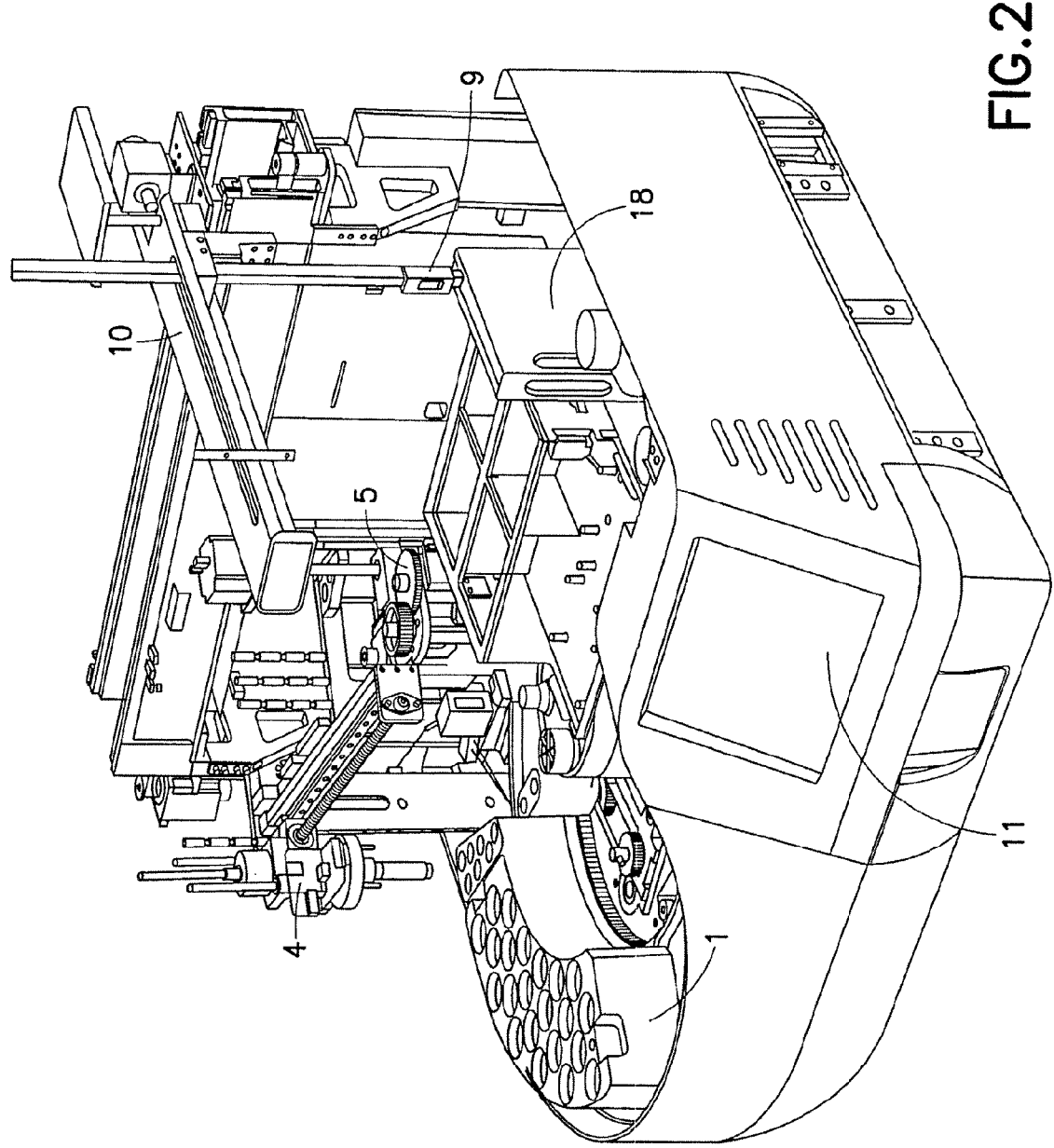
FIG. 2. Oblique view of the sample preparation system.
Figure 5A:
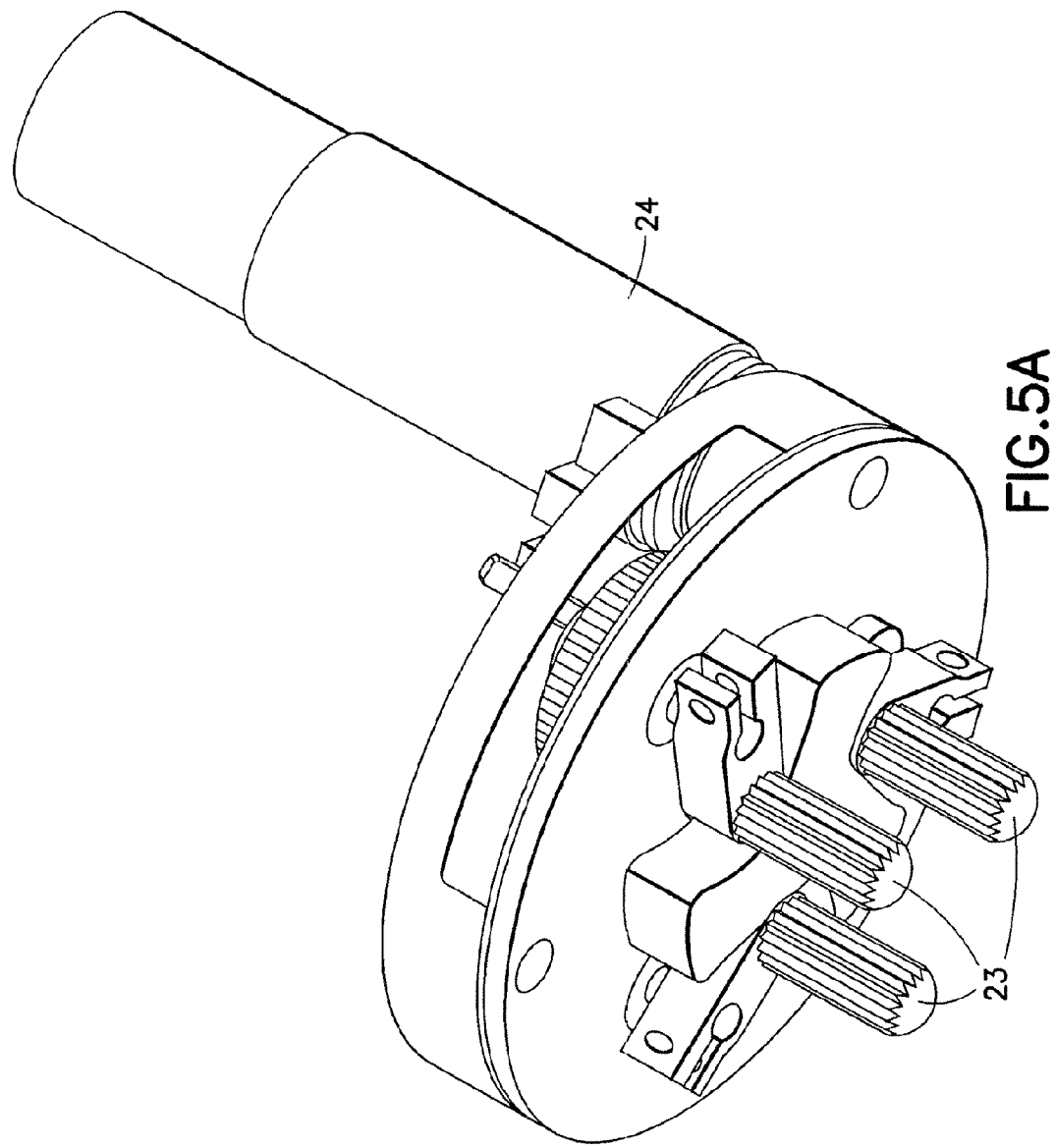
Figure 5B:
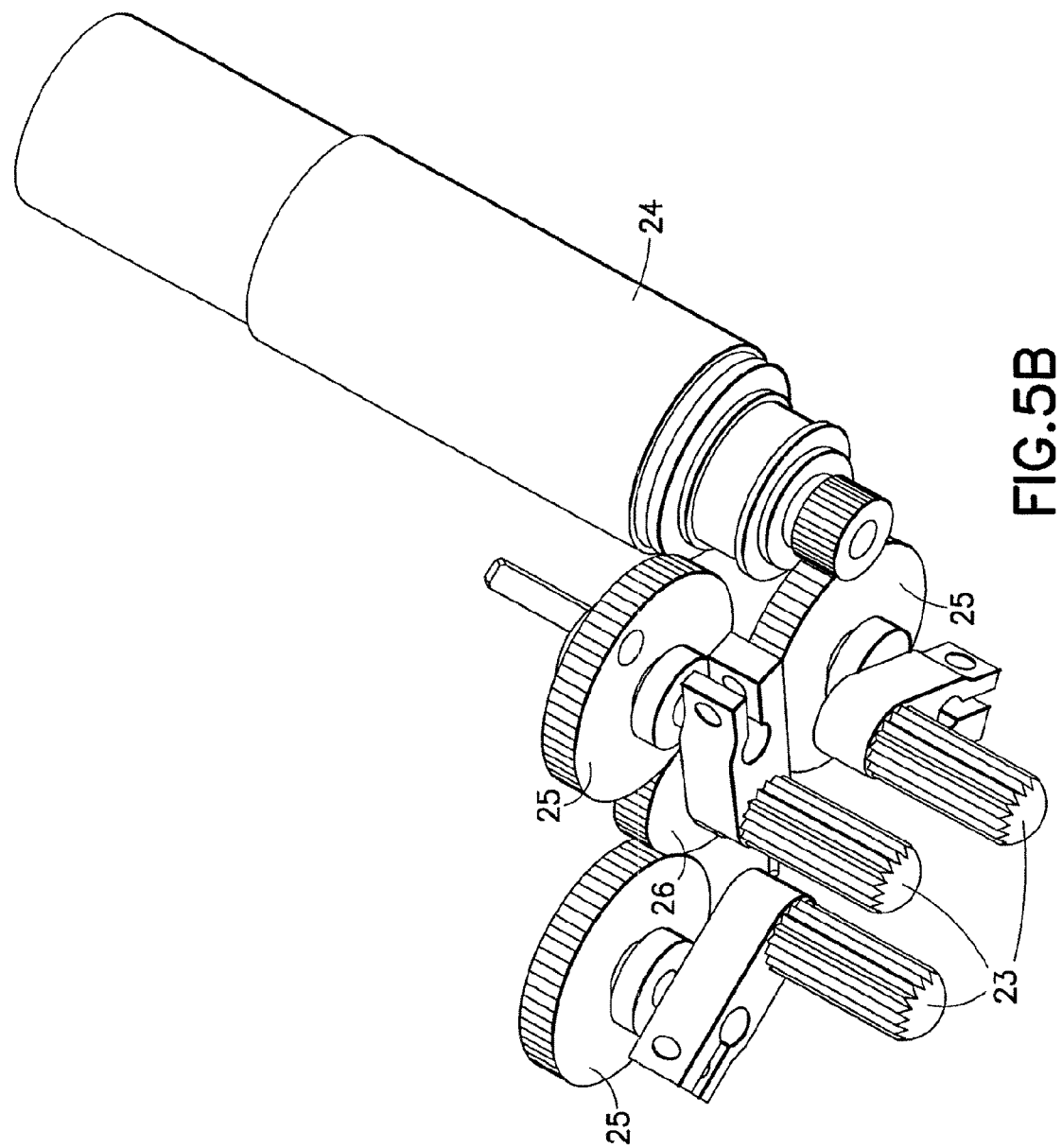

Referring to FIGS. 1 and 2, the vial handler arm 4 comprises a vial gripping assembly mounted on a vertical drive mechanism that raises and lowers the assembly. As illustrated in FIGS. 5A and 5B, in one embodiment, the vial gripping assembly comprises three gripping fingers 23 spaced equidistantly, radially and angularly around an axis where the gripping fingers are able to come together concentrically to grasp the cap of a vial 12. The vertical drive mechanism and vial gripping assembly is in turn mounted to a stationary arm where a lateral drive mechanism moves the whole assembly along the length of the arm. This allows the vial handler arm 4 to lower and grasp a vial, raise the vial from its location and to slide along the arm mount to another location and to lower and release the vial to a different location. The vial handler arm 4 grasps and transports vials between the input carousel, mixing basket, and staging carousel. The vial handler arm handles vials of any size and of multiple sizes in the same run or workflow of the SPS.

Mixing Basket

Referring to FIG. 1, vials may be mixed using the mixing baskets of the sample preparation system. The mixing basket comprises a basket for holding vials and an eccentric drive mechanism for agitating the basket. Activation of the drive shakes the mixing basket and the vials it is holding, resuspending the contents of the vials. Vials may be mixed by offset rotation of the mixing basket drive or by other known methods. The mixing basket may hold a plurality of vials of different sizes.

Staging Platform

The staging platform comprises at least one well for holding a vial and may comprise a plurality of wells for vial holding and vial gripping. The illustrative SPS incorporates a staging platform in the embodiment of a staging carousel having four wells. Each of the wells contains a vial gripping mechanism so that a vial cap can be removed from a stationary vial that is gripped by any of the wells. A drive mechanism rotates the staging carousel making vials accessible to the capper robotic arm 5 and for removal of an aliquot of the contents. A plurality of vial wells allows the handling of multiple vials and increases the number of processes that can be performed simultaneously, such as vial transfer, vial decapping/recapping and pipetting of vial contents. The staging platform may be any shape and is not required to be circular in shape or move. In an illustrative embodiment of the staging platform, the staging carousel is able to rotate or move vials to provide access to the capper arm 5, vial handling arm 4, and/or the specimen transfer pipette assembly. A single motor or actuator drives a cam that tightens a vial-gripping belt in the well of the staging platform. Rotation of the staging platform allows vial-gripping in the selected well or wells and allows all the wells to be capable of vial gripping through the action of a single motor or actuator. Additional motors, actuators, or cam arrangements may be used to tighten the vial gripping belt in more than one well at a time.

Additionally, the vial gripper belt is wound around the well in a counter-clockwise direction from a fixed end to a cam mounted end so that the belt has the property that it self tightens during decapping. Therefore, it can uncap vials that have been tightened to a range of torques up to the force limits of the capper. During recapping, the configuration of the vial gripper belt causes it to loosen at a predetermined torque setting insuring that the cap is recapped to a consistent torque.

Capper Arm

Vial caps are removed and replaced by the capper arm 5. An illustrative embodiment of a capper arm 5 comprises a capper module shown in FIGS. 5A and 5B, mounted on an arm located above the input platform 7 and staging platform 3. The module comprises a set of gripper fingers 23 that grasp the vial cap, a finger drive mechanism 24 to open and close the fingers, a rotational drive mechanism to rotate the gripper finger assembly, and a vertical drive mechanism to raise and lower the gripper finger assembly. The gripper fingers close by bringing together the three fingers concentrically toward the center of the gripper finger assembly via the finger drive mechanism 24. In alternate embodiments, the cap handler may comprise two opposing fingers that are capable of gripping a vial. To accommodate gripping a round cap, the fingers may be shaped appropriately or made of materials that allow sufficient frictional contact between the fingers and the cap. Curved fingers, fingers that are flexible, fingers coated with an elastic material are some examples that will allow a two-fingered cap handler to grasp a round cap. In yet other embodiments, the cap handler may comprise a one-finger assembly to grasp a vial. Such a finger may also comprise a loop or strap that may wrap around a cap and with tightening of the loop or strap grip the cap. Tightening of the loop or strap may be accomplished by rotation of the finger/cap handler or shortening of the loop or strap.

Decapping of a vial is done by rotating the staging platform containing a vial until the capper arm 5 is located above the capped vial. The staging platform well holding the vial tightens to grip the vial as the capper arm 5 lowers, grasps the vial cap, and rotates to uncap the cap. Once a vial is uncapped, the staging platform may be rotated to position the open vial under the specimen transfer pipette to allow access to the vial contents. As contents of the vial are removed, the cap may be held by the capper arm 5 until access to the sample contained in the vial is no longer needed. Recapping of the vial is performed when the vial is properly located below the capper arm 5. The process of decapping is reversed and the vial is recapped. Key parameters such as cap applied torque, cap insertion force, cap there/not there, cross thread sensing etc., may be measured by system sensors and may be adjusted by the operator and through a workflow control program. The capper arm can cap/decap vials of any size and of multiple sizes in the same run or workflow of the SPS. Vials containing run controls are frequently of a different size than sample vials.

In addition to turning caps to decap and holding caps during other processes of the SPS, the capper arm 5 is used to pick up vials and while holding them, rotate them so that a bar code scanner can read the bar code label on the vial.

Specimen Transfer Pipette Assembly

The specimen transfer pipette assembly comprises a tip head assembly 9 that can be lowered and raised and a pipette arm 10 to which the tip head assembly is mounted and that allows both X and Y axis movement and a detector 17. The pipette tip head assembly is connected via tubing to a pump that allows the controlled uptake and expulsion of liquids from the pipette. A detector or sensor 17 is attached to the tip head assembly 9 and allows the measurement/detection of fluid levels in a vial. The detector 17 may determine fluid levels by various methods such as optical, capacitive, impedance, vibration, pressure, radar/microwave, radio frequency, conductivity, resistance or ultrasonic/sonic. Sensors that do not require contact with the sample may also be used in determining the location and presence of objects within the SPS, such as disposable pipette tips, reagent bottles, waste bottles and destination receptacles. Any combination of the various methods may be used by a detector or detectors to perform measurement/detection and/or determining the location of objects within the SPS. An ultrasonic detector is used in an illustrative embodiment of the SPS. Any suitable ultrasonic detector can be used in this embodiment, such as those available from Cosense, Inc., Hauppauge, N.Y.

Removal of liquid sample from an uncapped vial is performed using a pipette arm assembly which loads a standard disposable pipette tip onto the tip head assembly 9. The tip head assembly is able to move to various locations in the SPS: to pickup a pipette tip, to remove an aliquot of sample from the vial, to place the aliquoted sample from the pipette into a sample processing tray or assay plate, and to eject the used tip into a waste tray. A pipette tip is picked up by movement of the tip head assembly 9 down onto an available pipette tip, where it is held by the tip head assembly 9 through friction with the nozzle 14.

Depending upon the vial size, liquid level in the vial is determined prior to pipetting or prior to picking up a pipette tip. If a sufficient amount of liquid is present, based upon measurement by the ultrasonic detector, the vial contents may be pipetted. Insufficient levels of liquid will generate an error message. Overfilled liquid levels will also generate an error message as this is usually indicative of sample tampering.

A microprocessor or programmable computer can be used to control every aspect of the operation of the SPS. Assay data is entered into the computer by touch screen monitor 11, keyboard, and handheld and built-in barcode scanners. Each of the subassemblies of the SPS may be controlled by its own microprocessor or computer, including the previously detailed assemblies and additionally the pumping assembly, heating mechanism, and bar code readers. A logic control circuit, microprocessor, central microprocessor or any one or more combination of these may be used to control an SPS subassembly.

An SPS will have at least one of each of the above components. However, additional copies of each of the above components will increase the throughput of the processor and may be used in embodiments of the SPS.

Data entry and function of the SPS are entered using a touch screen monitor 11, hand-held bar code reader and a keyboard. Information is displayed on the front panel display 11 of the instrument. Information is processed by an onboard microprocessor and is stored locally and can be stored on networked devices. Additionally, a barcode reader may be supplemented or replaced with an RFID reader and the use of RFID tags.

Operation of an Illustrative SPS

Typical functions performed by an illustrative SPS to process a single vial are described below.

After a program is initiated, the vial handling arm 4 moves toward the input platform rack 1 to obtain a vial. The vial handling arm 4 lowers, grips and lifts a vial, which is then positioned into the mixing basket. The mixing basket resuspends the vial contents. The vial handling arm 4 removes the shaken vial from the mixing basket and places the vial into the four-well staging platform.

Rotation of the staging platform moves the vial into a position accessible to the capper arm 5. The capper arm 5 lowers to grasp the vial. If the vial label was not read earlier by the primary bar code scanner that scans vials as they are transported from the input platform rack 1 to the mixer, the vial is pulled from the staging platform well and rotated in front of a barcode scanner to read the label and then returned to the well of the staging platform. While the capper arm 5 is holding the vial cap, the staging platform grasps the vial, sufficiently immobilizing it. The capper arm 5 rotates and removes the vial cap. With the vial cap removed, the staging platform rotates to allow removal of a sample from the vial.

The specimen transfer pipette assembly moves the tip head assembly 9 to a pipette tip storage box located in the holding area 8 and picks up a pipette tip. With a pipette tip in place, the specimen transfer pipette assembly moves over and above the uncapped vial. The ultrasonic volume detection sensor on the specimen transfer pipette assembly determines surface height and content sufficiency of the uncapped vial contents. The pipette tip head assembly is lowered into the vial and aspirates a measured amount of sample. A predetermined volume of sample is drawn into the pipette tip using a volumetric pump in communication with the pipette tip via a tube. The tube and volumetric pump may preferably be at least partially filled with a substantially incompressible fluid, such as water, and preferably only has gas in a portion of the tube to create gaseous interface between the sample drawn into the pipette tip and the hydraulic fluid in the tube. This arrangement preferentially assists in drawing a precise and predetermined volume of liquid by reducing total compressibility of the gas and liquid in the tube which is used to draw up the sample. Other means for drawing a predetermined volume include measuring the level of liquid using a fluid level sensor as a sample is withdrawn or measuring liquid level before and after a sample is withdrawn.

With an aliquot of sample contained in the pipette tip, the specimen transfer pipette moves to a destination plate where the specimen is dispensed into a plate well. The specimen transfer pipette then moves to and dispenses any remaining fluid into the system waste bottle. After all liquid is expelled, the specimen transfer pipette moves to the tip waste drawer where the used pipette tip is removed.

After an aliquot of the vial contents has been sampled, the staging platform moves to the recapping position. The vial cap that has been held by the capper arm 5 during aliquot sampling is secured back onto the vial. Once the vial is recapped, the staging platform moves to the vial pick-up position. The vial handling arm 4 lowers, grasps the vial, lifts the recapped vial and returns it to its original input platform rack well location.

Because the capper arm 5 holds the vial cap during aliquot sampling and does not place the vial cap down onto a surface, no cross-contamination of samples occurs through vial cap contact. By eliminating cross-contamination, recapped vials may be stored, archived, and resampled.

Rotation of the input platform rack 1 advances other vials into position to be processed. Several of the above operations of the SPS can be performed concurrently, including transfer of vials, resuspension of vial contents in the mixer, decapping/recapping, and aspirating/dispensing. With the completion of a run, the volume of sample dispensed in each destination receptacle may be verified by the ultrasonic detector scanning the detection plate for correct volume.

Example 1

An illustrative sample preparation system comprises an input platform for holding a plurality of vials. The input platform is shaped to receive individual removable segments wherein vials may be loaded prior to placement of the input rack segments into the processor. Up to 88 20 ml vials containing specimens collected in a collection medium or 176 10 ml vials containing specimens collected in a transport medium may be loaded into input racks and placed onto the input platform of the instrument for processing, including transport to the appropriate destination plate(s). The sample or specimen medium may be PRESERVCYT or SPECIMEN TRANSPORT MEDIUM. The destination plates may be 96-well microplates or 96-deep well filtration plates, depending upon the amount of the specimen. Typically, samples from 20 ml vials may be processed onto the deep well filtration plates while samples from 10 ml vials are processed onto the microplates. The input platform and input platform racks are not required to be circular and may be any shape and may move in any fashion such that the vials are accessible to the various components of the SPS. Additionally, the input platform and input platform racks may be stationary, with access to the samples provided by the movement of the robotic arms.

In operation, a vial handling arm 4 moves to an input platform 7 containing calibrator/control or samples/specimens. The vial handling arm 4 grasps and lifts a vial, which is then positioned into a vortex mixer. The vortex mixer resuspends vial contents. After vortex mixing, the vial handling arm 4 places the vial into a four-well staging platform 3. On transit to the staging platform 3 via the vial handling arm 4, the vial barcode may be read by a bar code scanner positioned between the input platform 7 and the staging platform 3. Rotation of the staging platform 3 moves the vial into a position accessible to a capper arm 5.

If the vial barcode was not read earlier, the capper arm 5 grasps the vial, pulls it from the well of the staging platform 3, if necessary to expose the bar code on the vial, and rotates it, allowing a barcode scanner to read the bar code, typically on a vial label. After placing the vial back into the staging platform well, a belt is tightened or tensioned around at least a portion of the circumference of the vial to stabilize the vial in the staging platform 3 while the capper arm 5 grasps the cap of the vial and removes the vial cap by rotating the cap in an opening direction. After the vial cap is removed, the staging platform 3 rotates the vial out from under the capper arm 5 to allow access for a specimen transfer pipette to remove sample or specimen from the vial. The capper arm 5 holds the cap while the sample or specimen is removed from the vial.

The tip head assembly 9, mounted on an X-Y-Z robot arm 10, moves to the tip box, lowers the tip head assembly into a disposable specimen tip staging area, and picks up a disposable specimen tip. A sensor confirms that the disposable specimen tip was successfully picked up. With the disposable specimen tip in place, the tip head assembly 9 moves over the uncapped vial in the staging platform. An ultrasonic volume detection sensor on the tip head assembly 9 determines surface height and sufficiency of the volume of the contents of the uncapped vial. As samples to be processed by the SPS may have been sampled earlier for analysis, measuring the amount of sample remaining allows tracking of the sample. The specimen transfer pipette assembly lowers the tip head assembly 9 until the disposable specimen tip is down into the vial specimen and aspirates a portion of the sample or specimen. With the sample contained in the disposable specimen tip, the specimen transfer pipette assembly moves the tip head assembly to a destination plate where the specimen is dispensed into a plate well. The tip head assembly then moves to and dispenses any remaining fluid into a system waste bottle. After all liquid is expelled, the tip head assembly moves to a sensor that confirms that the disposable specimen tip has not been dropped in transit and ejects the disposable specimen tip into a tip waste drawer.

After a sample has been removed, the staging platform moves to a recapping position. The vial cap that has been held by the capper arm 5 during sample removal is placed back onto the vial by rotating the cap in a closing direction. Once a vial is recapped, the staging platform moves to a vial pick-up position. The vial handling arm 4 then lifts the recapped vial and replaces it in the original calibrator/control or specimen input platform position. Rotation of the input platform advances other vials into position to be processed. After sampling an aliquot, all samples are recapped and returned to the input platform for storage, archiving, and/or resampling for further tests.

With the completion of a run, the volume of sample dispensed in each destination plate may be verified by the ultrasonic detector scanning the destination plate for correct volume.

Several of the above operations of the SPS can be performed concurrently on multiple vials, including transfer of vials, bar code reading, resuspension of vial contents in the mixer, decapping/recapping, aspirating/dispensing, and volume confirmation.

The processing of samples and specimens is controlled by an operator through a graphical user interface (GUI) control of the central microprocessor controlling the functions of the SPS. This allows the selection of the number of plates, plate layout, mixing time/speed, aspiration/dispense volume, and other assay protocol and control parameters by the operator.

Once the processing program is initiated, the processing of samples continues until completion. Error recovery sequences are incorporated at each step of the processing of samples and automatically resolve any mechanical problems during a run or, if operator intervention is required, halt the instrument's moving parts and emit an audible alarm and visual message in order to draw the operator's attention.

Several operator-selectable workflow programs are available on the SPS. These workflow programs specify the parameters that govern plate layout and transfer processes, including parameters such as destination receptacle type, calibrator/control parameters (e.g., type, number of dispenses), external control parameters (e.g., type, min/max ratios, % CV, destination receptacle layout (e.g., location in receptacle for calibrators/controls, specimens designated for initial testing or retesting, external controls), vial size, cap type, mixing time and speed, aspirate/dispense volume, retest replicates, as well as whether or not manually pipetted specimens are allowed.

Workflows are specific to an assay protocol, specimen type, and processing method. New workflows can be added to the SPS as new assay protocols are developed. Custom workflows can be created by an operator to meet a laboratory's unique testing requirements. More than one workflow can be selected for the same specimen type and can be selected for one SPS run. As an example, Digene High Risk UPV and Low-Risk UPV protocols can be run for the specimens.

The SPS tracks on-board consumables such as the system fluid bottle, reagent bottles 13, system waste bottle, biohazard waste bottle, tip boxes (e.g., number of tips and tip boxes needed to complete operator-selected workflow) and tip waste. Usually before a workflow is initiated, the SPS can notify the operator if consumables need to be replenished or if bottles and tip waste need to be emptied.

The SPS can prompt the operator through the loading of calibrators, controls and specimens, including prompts for: barcode scan of calibrator and control vials, loading calibrators/controls into an input platform, barcode scan of specimen-containing input platforms (e.g., confirmation of platform type for expected specimen type), loading input platform racks onto deck, loading destination plate(s), and confirming destination plate identity by barcode or other identifier.

Positive identification of various components of processing is accomplished by computer tracking of calibrator, control, specimen, and plate identification numbers. Specimen rack identification, specimen rack position, plate identification, and well position are associated with calibrator, control, and specimen identification. This information is shared with other software and/or downstream automated molecular assay systems for full tracking of vial-to-dispensed specimen and specimen-to-measured result.

Operator entry of calibrator, control, specimen rack, and plate identification prior to loading may be entered using an external, hand held barcode scanner. Identification may also be entered using the retractable keyboard on the front of the instrument. Internal barcode scanners of the SPS read identification during transport of the vials from the input platform to the staging platform.

Once a run is completed, the SPS transfers a file containing a map of the destination plate which corresponds to the processed samples to instruments downstream of the SPS or networked servers or drives. The plates processed by the SPS are then removed for further processing.

Data is transferred between one or more SPS and one or more molecular analysis system controllers, analyzers, or computers (e.g., PCs) connected through a network where the data is placed on a shared network server or data disk. The SPS may poll the network server or disk for data, which may include specimen identification requiring retesting, assay protocols, workflows, external controls added to the molecular analysis system software and ancillary shared data with downstream molecular assay systems. Molecular analysis system controllers, analyzers, or computers (e.g., PCs) may poll the network server or disk for destination plate map files. The SPS additionally comprises a USB port for data backup and/or for manual transfer of destination plate map data to molecular analysis system controllers, analyzers, or computers (e.g., PC). During operation, the SPS records run history and error events automatically. Thus, through software tracking of sample placement, the chain of custody can be maintained.

Cervical samples to be analyzed for UPV by a molecular diagnostic assay such as HYBRID CAPTURE 2 (HC2) may be manually processed or automatically processed using the RAPID CAPTURE SYSTEM instrument. In addition, various containers or vials with different types of screw caps can be used, with the capper arm 5 able to uncap the cap, hold the cap, and recap the vial.

The SPS is a component in a scalable testing system. It functions as a standalone unit, as a module in a networked configuration with one or more SPSs, as a module in a total laboratory automation system, or in other systems containing multiple components. As an example, additional devices such as downstream automated molecular assay systems may be included in a network or system.

Example 2

To increase the throughput of processing samples, the SPS can read barcodes and other identifying information on vials during the transit from the input platform to the vortex mixer, or from the vortex mixer to the staging platform for cap removal. In an illustrative SPS, while the vial is held by the vial handling arm 4 and moving toward the staging platform, the vial passes a bar code reader which reads the vial bar code. Reading of the bar codes in this manner may be facilitated by orienting the bar codes in the input platform rack during the operator loading of vials. Marks are located on the input platform racks to aid in orienting the vial bar codes so that they may be easily read by the bar code reader. If the barcode of the sample vial is not read before it reaches the staging platform, the capper arm 5 will pick up the vial after it has been placed in a well of the staging platform and rotate it so that a barcode reader can read it. To increase throughput in the handling of samples, the orientation of lining up sample barcodes may be automated. Automation may comprise lugs or indentations of the vial so that only a particular orientation of the vial that is optimal for barcode reading is possible within the input platform.

Example 3

In one of the sample processing operations of an illustrative SPS, there may be a need to further disperse a specimen prior to removal of a sample from a decapped vial. To aid in this process several different approaches may be required to ensure adequate specimen dispersion and distribution.

A reagent that helps disperse the specimen may be added to the vial contents. Such a reagent would ensure that sufficient amounts of the specimen are resuspended and can be aliquoted. After a vial is decapped, a measured quantity of dispersal reagent is pipetted from a reagent bottle 13, added to the vial, and the vial recapped. During the addition of the dispersal agent, the sample may be hydraulically mixed by repeated suction and expulsion of the suspension. An aliquot may be removed after the hydraulic mixing and transferred to a destination receptacle. If further mixing is required, the recapped vial is placed in the vortex mixer and agitated. From there, the vial can be decapped and an aliquot transferred to a destination receptacle. If time is needed to allow the reagent to work, any time after the addition of reagent the recapped vial may be returned to the input platform and allowed to incubate while another vial is processed. The order of the steps described above may be varied and their duration controlled by the SPS computer running the work flow program.

The reagent may be any solution suitable for dispersal of a medical or cytological specimen. Suitable reagents include, for example, any strong base, such as NaOH, KOH, and LiOH. Reagents may also include various detergents such as SDS, TRITON X-100, Brij-35, TWEEN-20, NP-40, and octylglucoside.

Example 4

In an automated diagnostic system, disposable pipette tips of various volumes are used to transfer various volumes of sample or specimen, to facilitate use of various sized sample or specimen vials or containers, and to prevent sample carryover. In an illustrative sample preparation system, the disposable pipette tips are picked up accurately, sealed to the tip head assembly, and retained during aspiration/dispensing of various fluids until removed by the sample preparation processor.

Figure 3A:
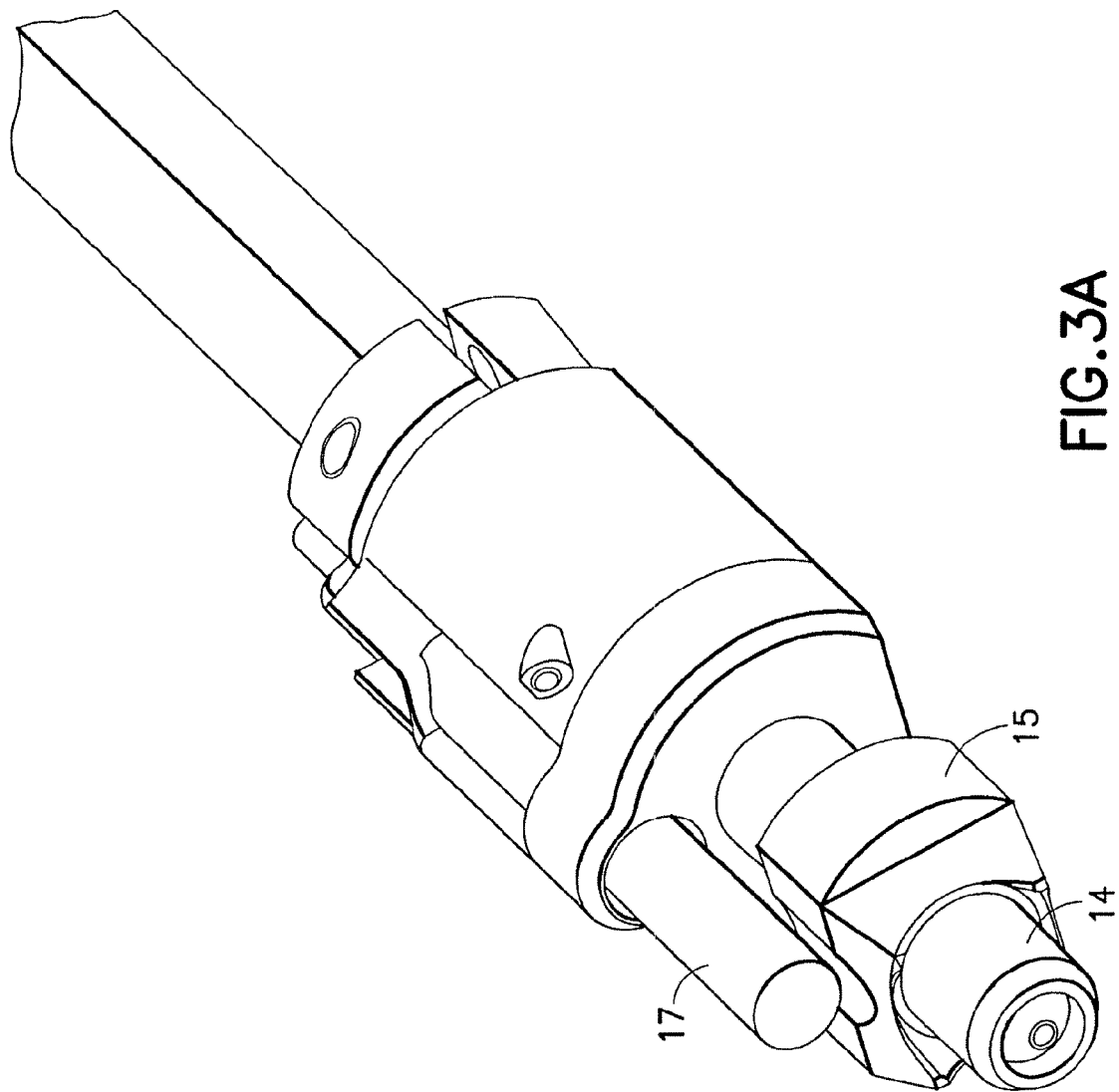
FIG. 3A. Tip Head Assembly
FIG. 3B. Tip Head Assembly
FIG. 4A. Staging Platform (Carousel) Assembly
FIG. 4B. Staging Platform (Carousel) Assembly
FIG. 5A. Cap Gripping Assembly
FIG. 5B. Cap Gripping Assembly

A self centering tip holder mechanism aligns the tip head assembly to the disposable pipette tip to accurately center the tip head assembly to the disposable tip prior to the tip head assembly being lowered to pick up a disposable pipette tip. (FIGS. 3A and 3B). A spring loaded compliance 16 is built into the tip head assembly to allow the stepper motor to insert the nested nozzle tip 14 beyond the predicted stop. This ensures a fluid tight seal when attaching the nested nozzle tip to a disposable pipette tip, without step loss from the stepper motor or damage to the disposable tip.

A slideably mounted alignment collar attached to the nested nozzle tip 14 of the tip head assembly helps to align the nested nozzle tip 14 to a disposable tip. The collar is retained using a shoulder screw and slides down over the nested nozzle tip when a disposable tip is not in place. When the specimen transfer pipette retrieves a disposable tip, the alignment collar which has a taper receiver aligns the disposable tip within the nozzle tip of the tip head assembly 9 with engages the disposable tip. The collar 15 corrects any larger misalignment of the tip head assembly prior to engagement of the disposable tip by the nested nozzle 14 and a beveled edge of nested nozzle 14 corrects any minor misalignments.

The nozzle tip has compliance in that a spring 16 is used which keeps the nozzle tip extended. As the nozzle tip retrieves a disposable tip, the nozzle compresses, applying a given amount of force into the disposable tip creating a tight seal for fluid aspirating/dispensing without losing motor steps or damage to the disposable tip.

Other methods of alignment of a disposable tip that may be used in illustrative sample preparation systems include taper of the nozzle tip barrel or beveled edge. This taper or bevel helps guide the tip head assembly 9 to the disposable tip for pickup. Use of filtered disposable tips limits the amount of taper that can be used in retrieving such a tip. This makes alignment more difficult when retrieving filtered disposable tips from a disposable rack.

The alignment collar 15 is also used in ejecting pipette tips. Pipette tips are ejected from the tip head assembly 9 when the alignment collar is placed under the two top edges of the tip disposal chute 18 followed by the XYZ arm 10 raising the tip head assembly 9 up in the Z direction. While the alignment collar 15 is held by the edges of the tip disposal chute 18, force is applied to the pipette tip by the alignment collar 15 from the upward motion of the nested nozzle tip 14 with the raising of the tip head assembly 9. The nested nozzle tip 14 then pulls free from the pipette tip, which drops into the waste drawer below.

Example 5

Staging Platform Assembly

Figure 4A:
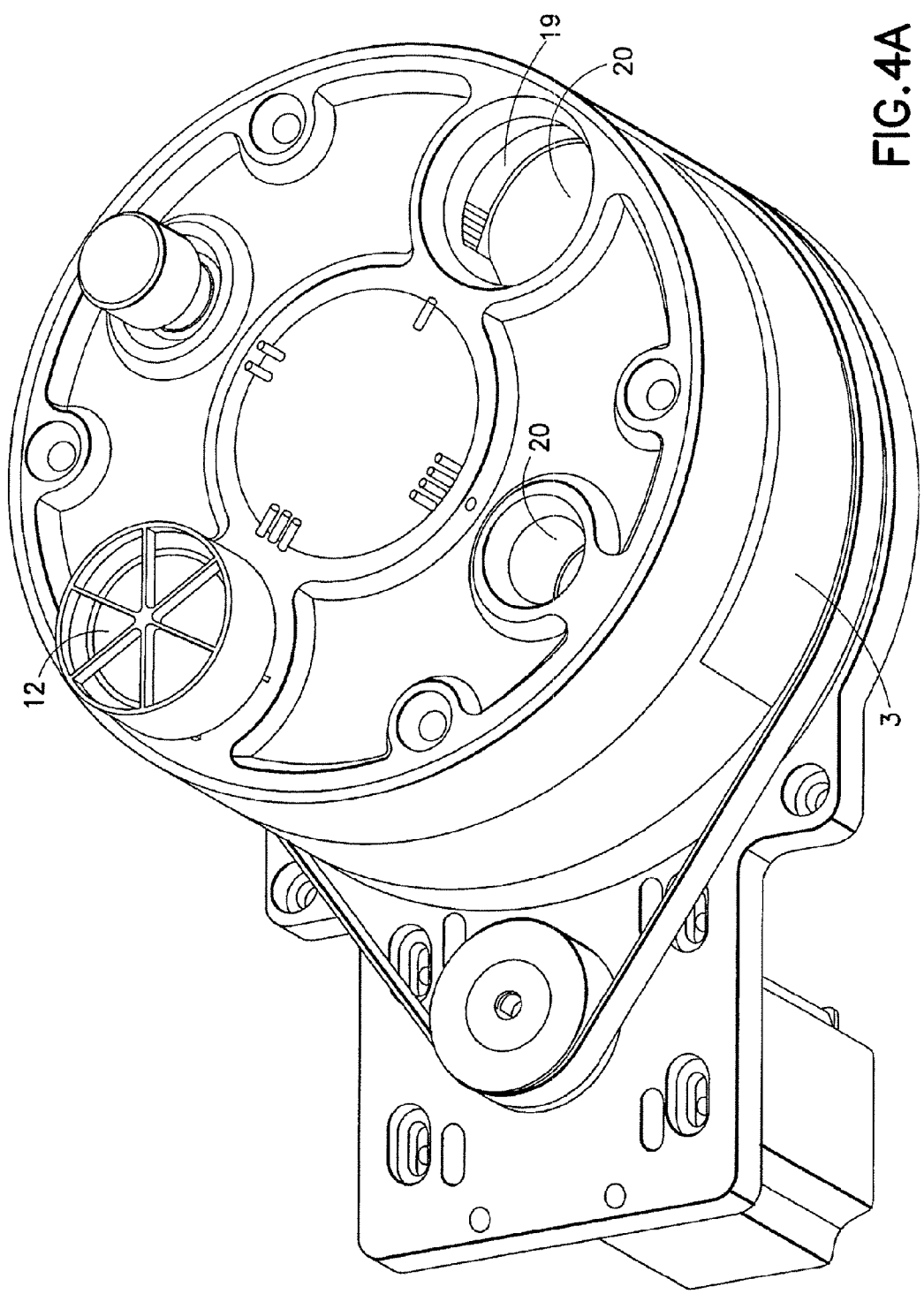
Figure 4B:
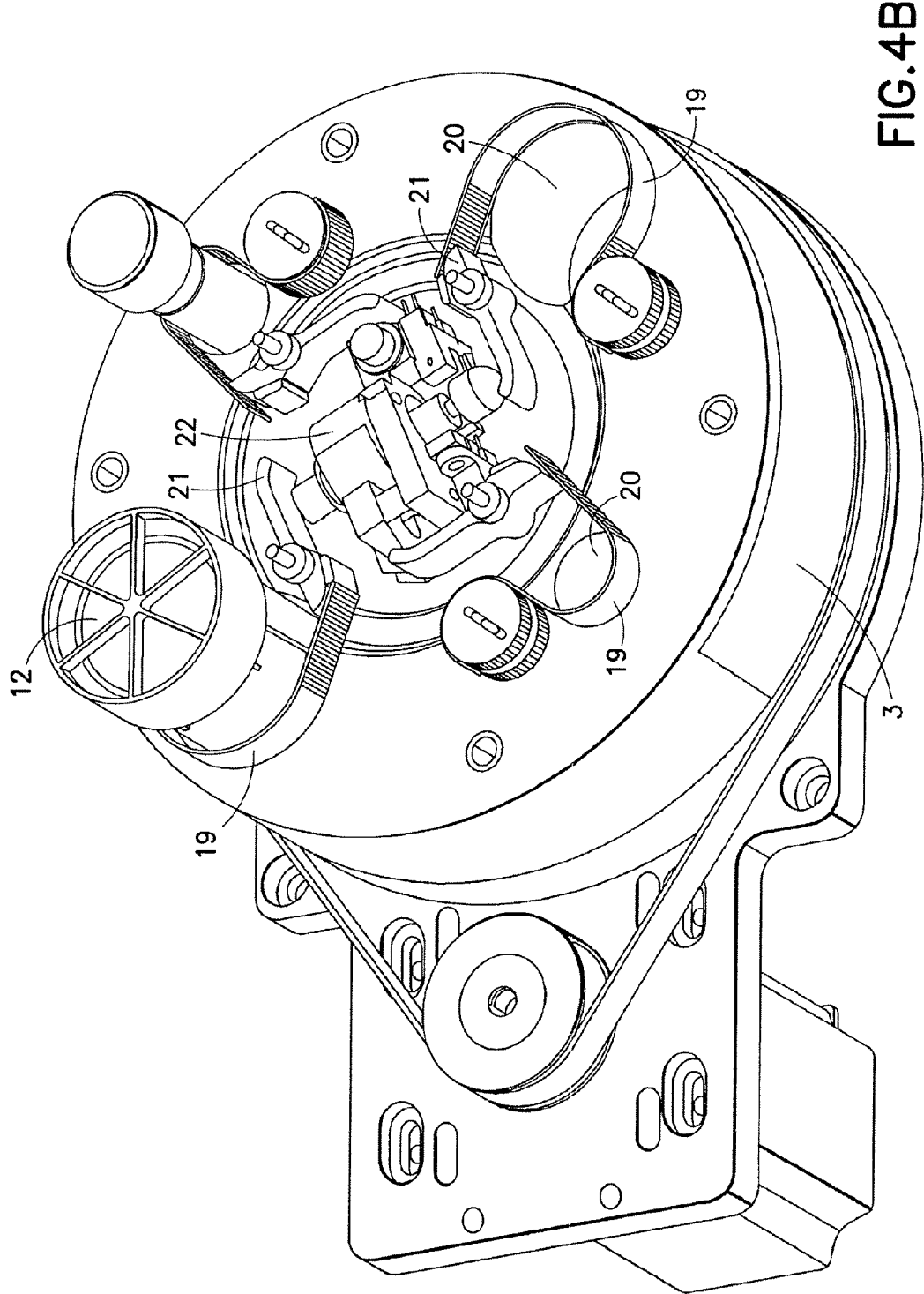

In an illustrative sample preparation system, the staging platform functions, in part, by holding a vial in its wells with a belt to prevent the vial from rotating or coming out of the well during decapping and recapping (FIGS. 4A and 4B). A known pressure/force is applied to the belt to hold the vial and prevent it from rotating or being lifted.

In medical diagnostics, various sizes (e.g., diameters) and shapes of containers are used that contain various types of samples, and specimens, typically in the form of a fluid or as solids or other material suspended or stored in a fluid. These fluid samples and specimens must be safely stored in the vial or container and accessed safely for transfer to a destination receptacle or other processing. A vial is gripped so that the sealing cap can be removed and reapplied safely without spillage during retrieval of specimens. The automated decapping and recapping prevents spillage before and after the retrieval, transfer, or processing of samples or specimens.

In the staging platform 3, a spring mounted to a belt cam 21 keeps the belt 14 from closing prematurely onto the vial or into an empty well. After a vial is placed into the sample holder well of the staging platform, a motor 22 is actuated that applies a force to the belt cam which tightens or tensions the belt around at least a portion of the circumference of the vial. The belt is advantageously mounted in a direction that allows the belt to tighten or tension as a vial is decapped. When the force is reversed or when the cap is recapped onto the vial, the belt slips around the vial after a given force is applied.

When the staging platform prevents the vial from rotating, a motor applies a force to a cam which tightens the belt around the vial. This force applied to the belt is limited using a spring attached to the motor mount that pivots when a given force is applied. Attached at the end of the motor shaft is an actuator cap which contacts the belt cam which tightens or tensions the belt around at least a portion of the circumference of the vial. When a given force is reached, the actuator mount to which the motor is attached begins to rotate, applying a compressing force to the spring that actuates a sensor.

A staging platform may also grasp vials or containers by various other methods. A claw mechanism may grasp the vial. The vial or container may be forced against the well wall of the platform by a rod, cam, plate, or strap. The vial is held by the force of an object pressing against it within the well perpendicular to the tangent of the vial circumference. With indentations or special lugs on the vial/container, a well with mating surfaces to the indentations or lugs would hold the vial/container stationary.

Example 6

Cap Gripping Assembly

In an automated diagnostic system, various sizes of vials are usually capped to retain fluid specimens for transport from the clinic or testing site to the analysis laboratory. These caps must be removed to aspirate the fluid within the vial. After an amount of fluid is removed, using a given amount of force, the cap can be tightened back onto the vial to prevent the fluid from spillage and to preserve the sample or specimen for further testing, repeat testing, or archiving.

The cap gripping mechanism of an illustrative sample processing system grips a vial cap through means of a spring/sensor feedback system (FIGS. 5A and 5B). The gripping force can be a constant force, but need not necessarily be constant provided that the force is sufficient to effect the decapping and recapping processes. A cap is gripped by the gripper mechanism of the capper arm 5. The gripper effects a force on the cap at three points in order to constrain the cap in the theta direction. Constraint of the cap in the theta direction allows for decapping and recapping of the cap.

The gripper mechanism comprises a top and bottom housing into which bearings are pressed. Between the housings are three output shafts that are supported by the bearings. Each shaft has a gear 25 and located in the center is a gear 26 that couples each of the output shafts to provide synchronized motion. A gear motor 24 with a pinion gear drives the gears and effects torque on the output shafts. Three gripper fingers 23 are attached to the output shafts. Each gripper finger has a pin (knurled or serrated, depending on the application requirement) that interfaces with the cap directly and effects normal force along that interface.

The rotation of the output shafts allows the gripper fingers to open and close. The torque of the motor is transmitted to the fingers by the gear set. When the fingers hit a relatively immovable object, such as the cap, the reaction torque is limited by means of a torque sensor. This torque sensor is a binary sensor that changes state when the moment on the arm exceeds the force of a limiting spring. The torque at which the sensor actuates is directly proportional to the stiffness of the limiting spring. The gear motor is mounted in a pivot which passes through two support bearings and allows the motor to spin freely about its axis. The pivot has an arm which extends from the center and to which a spring attaches. The other end of the extension spring is attached to the top of the housing. With the preload of the spring applied, the arm rests against a hard stop. In this position, an optical switch is blocked by the presence of the arm. When the gripper fingers are in contact with the cap, motion is limited as a result, the motor turns on its pivot against the force of the spring. The optical sensor detects the motion of the arm. In this fashion, any size cap can be gripped with sufficient force to effect the decapping and recapping processes without crushing the cap. The cap gripper mechanism can be used for uncapping and recapping different sized vial caps and allows the SPS to handle different-sized vials in the same run or workflow.

Example 7

Sample Temperature Control

Temperature control of samples to be processed is accomplished using heating/cooling units. These units are located beneath the input platform, in the input platform, in the destination receptacle holding area, and/or at any location within the SPS to facilitate temperature control. Methods of heating and/or cooling samples may be accomplished by the use of heating elements, water circulation, heated air, and Peltier-effect elements.

Similarly, reagents can be heated or cooled within the SPS, providing optimal temperature conditions for sample preparation reactions. Reagents may be heated and/or cooled by the use of heating elements, water circulation, heated air, and Peltier-effect elements.

Temperatures for all heating/and or cooling are monitored and under control of the SPS computer. Sensors for monitoring temperatures include IR sensors, thermocouples, thermoresistors, and semiconductor thermometers.

Example 8

Chemical separation of the sample components of a vial may include precipitation agents such as ethanol, methanol, ammonium sulfate, polyethyleneimine, polyethylene glycol, and antibodies (immunoprecipitation). Sample components may comprise cells, nucleic acids, virus particles, microorganisms, and/or proteins. Physical separation of samples may include centrifugation, filtration, binding to a matrix such as polyvinyl difluoridine or nitrocellulose, binding to silica beads, binding to magnetic silica beads, binding by antibody coated silica beads, or allowing contents of the vial to settle. Vial or container caps may be used that aid in concentrating the specimen and removing the preservative medium.

Example 9

An example of a molecular diagnostic assay may be an assay where information useful in determining the medical status of an individual can be obtained using molecular biology methods including but not limited to nucleic acid hybridization, antibody binding, ELISA, nucleic acid amplification, nucleic acid purification, nucleic acid sequencing, antigen or protein purification, protein sequencing, enzymatic treatment of nucleic acids, restriction enzyme digestion, enzymatic treatment of proteins, nucleic acid or protein electrophoresis, nucleic acid or protein blotting, measurement of enzymatic activity, chemical modification of nucleic acid, labeling of nucleic acid, chemical modification of protein, and labeling of protein. Accordingly, an example of a molecular analysis may be an analysis that uses molecular biology methods as described above.

An example of a specimen may be any material collected from a patient. This material includes but is not limited to any and all possible bodily secretions, fluids, cells, tissues, metabolites, and naturally occurring and synthetic compounds. Microorganisms, including bacteria and viruses associated with any of these materials would also be understood to be a specimen.

An example of a capped vial may be a container with a corresponding lid whereby the lid provides a seal sufficient to prevent a liquid contained in the capped container to leak and whereby the cap can be removed and replaced repeatedly to allow repeated access to a sample. The vial and cap may be made of any suitable material that can contain a liquid that will be used for a patient specimen. The vial and cap require no special indentations, extrusions, indexing, or reference marks to allow repeated decapping and recapping of the vial by the illustrative SPS.

Illustrative embodiments of the system may further include the following:

A vial processing system comprising an input platform adapted to receive a vial; a staging platform adapted to receive a vial; a vial handler positioned to transfer a vial between the input platform and staging platform; a cap handler positioned to engage and remove a cap of a vial in the staging platform; a vial gripper to restrict movement of the vial during removal of the cap; and a transfer pipette assembly comprising a pipette arm and tip head assembly, the tip head assembly being mounted to the pipette arm and adapted to receive a pipette tip, the pipette arm being positioned to translate the tip head assembly between an open vial and a destination area.

This illustrative embodiment may optionally include a vacuum generator in communication with the tip head assembly to withdraw a predetermined volume of fluid from a vial.

A further illustrative embodiment may optionally include a mixing basket adapted to receive a vial and wherein the vial handler is further positioned to transfer a vial between the input platform, staging platform and mixing basket.

In a further illustrative embodiment the input platform may optionally be adapted to receive a vial holding rack having a plurality of wells adapted to receive a plurality of vials.

A further illustrative embodiment may optionally include two vial holding racks, wherein the wells of a first vial holding rack are adapted to receive a first set of vials and the wells of a second vial holding rack are adapted to receive a second set of vials, and wherein the wells of the first vial holding rack have a different set of dimensions from the wells of the second vial rack.

In yet a further illustrative embodiment the vial gripper may optionally include a belt attached to the staging platform at one end and connected to a tightening lever arm at the other end to form at least a partial loop for receiving a vial, whereby the belt tightens around a vial disposed in the loop when force is applied to the lever arm.

A further illustrative embodiment is a specimen processing system similar to that described above wherein the cap handler comprises at least two fingers extending parallel to and substantially equidistance radially and angularly from a central axis, and a torque sensor for sensing the force of the fingers on a vial cap being engaged, whereby the cap handler is capable of engaging vial caps of variable size.

In addition, an illustrative specimen processing system may optionally have the tip head assembly aligned substantially parallel to the longitudinal axis of a tip head and comprises a collar, a beveled nozzle tip and a liquid level measurement sensor, wherein the collar is slideably attached to the nozzle tip and wherein the nozzle tip is compliant in the longitudinal direction.

A further illustrative embodiment is an automated specimen processing system comprising (1) a microprocessor; (2) an input carousel for receiving a plurality of semi-circular vial holding racks wherein the vial holding racks have a plurality of wells sized to receive a plurality of vials, and wherein the microprocessor is in functional communication with the input carousel and is capable of controlling the rotational movement of the carousel; (3) a mixing basket having a well sized to receive a vial wherein the microprocessor is in functional communication with the mixing basket and is capable of controlling the mixing of the contents of a vial; (4) a staging carousel having a plurality of wells sized to receive a plurality of vials and wherein the microprocessor is in functional communication with the staging carousel and is capable of controlling the rotational movement of the carousel; (5) a vial gripper comprising a belt having a first and second end and being disposed within each staging carousel well, a lever arm having a first and second ends, and an actuator, wherein the first end of the belt is connected to the staging platform, the second end of the belt is connected to a first end of a tightening lever arm, and the actuator is arranged to communicate with the second end of the lever arm, wherein the microprocessor is in functional communication with the actuator and is capable of controlling the engagement of the actuator with the lever arm and tightening and releasing of the belt on a vial; (6) a vial handler positioned to transfer vials between the input carousel, mixing basket and staging carousel wherein the microprocessor is in functional communication with the vial handler and is capable of controlling the movement of vials between the input carousel, mixing basket and staging carousel; (7) a cap handler positioned to engage a cap of a vial and to remove and reapply the cap to the vial, wherein the cap handler comprises at least two fingers extending parallel to and substantially equidistance radially and angularly from a central axis, and a torque sensor for detecting the force of a finger on a vial cap being engaged, whereby the cap handler is capable of engaging vial caps of variable size, and wherein the microprocessor is in functional communication with the cap handler and is capable of controlling the engagement of the cap handler with a vial cap; and (8) a transfer pipette assembly comprising a pipette arm, a tip head assembly, and a vacuum generator pump, the tip head assembly being mounted to the pipette arm and adapted to receive a disposable pipette tip, the pipette arm being positioned to translated the tip head assembly between a pipette tip storage area, an open vial, a destination plate and a pipette tip discharge area, wherein the tip head assembly is aligned parallel to the longitudinal axis of a tip head and comprises a collar, a beveled nozzle tip and a liquid level measurement sensor, wherein the collar is slideably attached to the nozzle tip and wherein the nozzle tip is compliant in the longitudinal direction, and wherein the microprocessor is in functional communication with the transfer pipette assembly and is capable of controlling the movement of the tip head assembly between the pipette tip storage area, the open vial, the destination plate and the pipette tip discharge, and is capable of controlling the operation of the vacuum generator pump to withdraw a predetermined volume of content from a vial.

An illustrative embodiment of the system includes a method of processing specimens comprising (1) placing a vial in an input platform adapted to receive the vial; (2) transferring a vial from the input platform to a staging platform adapted to receive a vial using a vial handler positioned to transfer vials between the input platform and staging platform under control of a microprocessor; (3) gripping the vial in the staging platform to prevent rotational motion and while gripping the vial, removing a cap from the vial using a cap handler positioned to engage and remove a cap of a vial under control of a microprocessor; (4) holding the cap in the cap handler while removing a predetermined volume of vial contents from the uncapped vial using a transfer pipette assembly comprising a pipette arm and tip head assembly, the tip head assembly being mounted to the pipette arm and adapted to receive a pipette tip, the pipette arm being positioned to translated the tip head assembly between an open vial and a vial content destination area under control of a microprocessor; (5) discharging the predetermined volume of content from the pipette onto a destination plate under control of a microprocessor; and (6) recapping the vial after the predetermined volume of content has been removed from the vial under control of a microprocessor.

The above description of various illustrative embodiments has been presented for purposes of illustration and description. It is not intended to be exhaustive or limiting to the precise forms disclosed. Obvious modifications or variations are possible in light of the above teachings. The embodiments discussed were chosen and described to provide illustrations and its practical application to thereby enable one of ordinary skill in the art to utilize the various embodiments and with various modifications as are suited to the particular use contemplated. All such modifications and variations are within the system as determined by the appended claims when interpreted in accordance with the breadth to which they are fairly, legally and equitably entitled.

What is claimed is:

1. A vial processing system comprising:
    an input platform adapted to receive a vial;
    a staging platform adapted to receive a vial;
    a vial handler positioned to transfer a vial between the input platform and staging platform;
    a cap handler positioned to engage and remove a cap of a vial in the staging platform;
    a vial gripper disposed on the staging platform to restrict movement of the vial during removal of the cap;
    a transfer pipette assembly comprising a pipette arm and tip head assembly, the tip head assembly being mounted to the pipette arm and adapted to receive a pipette tip, the pipette arm being positioned to translate the tip head assembly between an open vial and a destination area;
    and a mixing basket adapted to receive a vial and wherein the vial handler is further positioned to transfer a vial between the input platform, staging platform and mixing basket.

2. The vial processing system of claim 1, further comprising a vacuum generator in communication with the tip head assembly to withdraw a predetermined volume of fluid from a vial.

3. The vial processing system of claim 2, wherein the vacuum generator comprises a volumetric pump in hydraulic communication with the transfer pipette assembly.

4. The vial processing system of claim 3, further comprising a tube connecting the volumetric pump to the transfer pipette assembly, wherein a path formed by the tube, volumetric pump and pipette assembly is at least partially filled with a substantially incompressible fluid, and partially filled with a gas to create a gaseous interface between the substantially incompressible fluid and a sample volume drawn into the pipette tip from the vial.

5. The vial processing system of claim 1, further comprising an ultrasonic sensor positioned to detect fluid in an uncapped vial.

6. The vial processing system of claim 1, wherein the mixing basket further comprises an eccentric drive mechanism that agitates the basket and vial to resuspend contents of the vials.

7. The vial processing system of claim 1, wherein the mixing basket is adapted to receive a plurality of vials.

8. The vial processing system of claim 1, wherein the input platform is adapted to receive a vial holding rack having a plurality of wells adapted to receive a plurality of vials.

9. The vial processing system of claim 8, further comprising two vial holding racks, wherein the wells of a first vial holding rack are adapted to receive a first set of vials and the wells of a second vial holding rack are adapted to receive a second set of vials, and wherein the wells of the first vial holding rack have a different set of dimensions from the wells of the second vial rack.

10. The vial processing system of claim 1, wherein the vial gripper comprises a belt attached to the staging platform at one end and connected to a tightening lever arm at the other end to form at least a partial loop for receiving a vial, whereby the belt tightens around a vial disposed in the loop when force is applied to the lever arm.

11. The vial processing system of claim 10, wherein the belt is wrapped around a vial from the end connected to the staging platform to the end connected to the lever arm in the same direction as the direction of cap rotation used to remove a cap from a vial.

12. The vial processing system of claim 1, wherein,
the staging platform further comprises a plurality of wells sized to receive a vial and disposed along the perimeter of the staging platform, and
the vial gripper further comprises a belt disposed along the perimeter wall of each well, a lever arm attached to each belt, and an actuator arranged to communicate with the end of a lever arm, wherein,
each belt is attached at one end to the staging platform and at the other end to a lever arm,
each lever arm is disposed at the perimeter of each well with a free end of the lever arm disposed toward the center of the staging platform,
the actuator is disposed at the center of the of the staging platform in selective communication with the free end of each lever arm, and
the staging platform, wells, belts and lever arms are rotatable with respect to the actuator whereby the actuator can selectively communicate with a lever arm through rotation of the staging platform.

13. The vial processing system of claim 1, wherein the cap handler comprises at least two fingers extending parallel to and substantially equidistance radially and angularly from a central axis, and a torque sensor for sensing the force of the fingers on a vial cap being engaged, whereby the cap handler is capable of engaging vial caps of variable size.

14. The vial processing system of claim 13, further comprising a rotational drive engaging the cap handler for rotation of the cap handler about its central axis, whereby the cap handler can screw and unscrew a vial cap by actuating the rotational drive.

15. The vial processing system of claim 1, wherein the tip head assembly is aligned substantially parallel to the longitudinal axis of a tip head and comprises a collar, a beveled nozzle tip and a liquid level measurement sensor, wherein the collar is slideably attached to the nozzle tip and wherein the nozzle tip is compliant in the longitudinal direction.

16. A vial processing system comprising:
an input platform adapted to receive a vial;
a staging platform adapted to receive a vial;
a vial handler positioned to transfer a vial between the input platform and staging platform;
a cap handler positioned to engage and remove a cap of a vial in the staging platform;
a vial gripper disposed on the staging platform to restrict movement of the vial during removal of the cap, the vial gripper comprising a belt attached to the staging platform at one end and connected to a tightening lever arm at the other end to form at least a partial loop for receiving a vial, whereby the belt tightens around a vial disposed in the loop when force is applied to the lever arm; and
a transfer pipette assembly comprising a pipette arm and tip head assembly, the tip head assembly being mounted to the pipette arm and adapted to receive a pipette tip, the pipette arm being positioned to translate the tip head assembly between an open vial and a destination area.

17. The vial processing system of claim 16, further comprising a vacuum generator in communication with the tip head assembly to withdraw a predetermined volume of fluid from a vial.

18. The vial processing system of claim 17, wherein the vacuum generator comprises a volumetric pump in hydraulic communication with the transfer pipette assembly.

19. The vial processing system of claim 18, further comprising a tube connecting the volumetric pump to the transfer pipette assembly, wherein a path formed by the tube, volumetric pump and pipette assembly is at least partially filled with a substantially incompressible fluid, and partially filled with a gas to create a gaseous interface between the substantially incompressible fluid and a sample volume drawn into the pipette tip from the vial.

20. The vial processing system of claim 16, further comprising an ultrasonic sensor positioned to detect fluid in an uncapped vial.

21. The vial processing system of claim 16, further comprising a mixing basket adapted to receive a vial and wherein the vial handler is further positioned to transfer a vial between the input platform, staging platform and mixing basket.

22. The vial processing system of claim 21, wherein the mixing basket further comprises an eccentric drive mechanism that agitates the basket and vial to resuspend contents of the vials.

23. The vial processing system of claim 21, wherein the mixing basket is adapted to receive a plurality of vials.

24. The vial processing system of claim 1, wherein the input platform is adapted to receive a vial holding rack having a plurality of wells adapted to receive a plurality of vials.

25. The vial processing system of claim 24, further comprising two vial holding racks, wherein the wells of a first vial holding rack are adapted to receive a first set of vials and the wells of a second vial holding rack are adapted to receive a second set of vials, and wherein the wells of the first vial holding rack have a different set of dimensions from the wells of the second vial rack.

26. The vial processing system of claim 16, wherein the belt is wrapped around a vial from the end connected to the staging platform to the end connected to the lever arm in the same direction as the direction of cap rotation used to remove a cap from a vial.

27. The vial processing system of claim 16, wherein,
the staging platform further comprises a plurality of wells sized to receive a vial and disposed along the perimeter of the staging platform, and
the vial gripper further comprises a belt disposed along the perimeter wall of each well, a lever arm attached to each belt, and an actuator arranged to communicate with the end of a lever arm, wherein,
each belt is attached at one end to the staging platform and at the other end to a lever arm,
each lever arm is disposed at the perimeter of each well with a free end of the lever arm disposed toward the center of the staging platform,
the actuator is disposed at the center of the of the staging platform in selective communication with the free end of each lever arm, and
the staging platform, wells, belts and lever arms are rotatable with respect to the actuator whereby the actuator can selectively communicate with a lever arm through rotation of the staging platform.

28. The vial processing system of claim 16, wherein the cap handler comprises at least two fingers extending parallel to and substantially equidistance radially and angularly from a central axis, and a torque sensor for sensing the force of the fingers on a vial cap being engaged, whereby the cap handler is capable of engaging vial caps of variable size.

29. The vial processing system of claim 28, further comprising a rotational drive engaging the cap handler for rotation of the cap handler about its central axis, whereby the cap handler can screw and unscrew a vial cap by actuating the rotational drive.

30. The vial processing system of claim 16, wherein the tip head assembly is aligned substantially parallel to the longitudinal axis of a tip head and comprises a collar, a beveled nozzle tip and a liquid level measurement sensor, wherein the collar is slideably attached to the nozzle tip and wherein the nozzle tip is compliant in the longitudinal direction.

31. A vial processing system comprising:
an input platform adapted to receive a vial;
a staging platform adapted to receive a vial, the staging platform comprising a plurality of wells sized to receive a vial and disposed along a perimeter of the staging platform;
a vial handler positioned to transfer a vial between the input platform and staging platform;
a cap handler positioned to engage and remove a cap of a vial in the staging platform;
a vial gripper disposed on the staging platform to restrict movement of the vial during removal of the cap, the vial gripper comprising a belt disposed along the perimeter wall of each well, a lever arm attached to each belt, and an actuator arranged to communicate with the end of a lever arm; and
a transfer pipette assembly comprising a pipette arm and tip head assembly, the tip head assembly being mounted to the pipette arm and adapted to receive a pipette tip, the pipette arm being positioned to translate the tip head assembly between an open vial and a destination area, wherein,
each belt is attached at one end to the staging platform and at the other end to a lever arm,
each lever arm is disposed at the perimeter of each well with a free end of the lever arm disposed toward the center of the staging platform,
the actuator is disposed at the center of the of the staging platform in selective communication with the free end of each lever arm, and
the staging platform, wells, belts and lever arms are rotatable with respect to the actuator whereby the actuator can selectively communicate with a lever arm through rotation of the staging platform.

32. The vial processing system of claim 1, further comprising a vacuum generator in communication with the tip head assembly to withdraw a predetermined volume of fluid from a vial.

33. The vial processing system of claim 32, wherein the vacuum generator comprises a volumetric pump in hydraulic communication with the transfer pipette assembly.

34. The vial processing system of claim 33, further comprising a tube connecting the volumetric pump to the transfer pipette assembly, wherein a path formed by the tube, volumetric pump and pipette assembly is at least partially filled with a substantially incompressible fluid, and partially filled with a gas to create a gaseous interface between the substantially incompressible fluid and a sample volume drawn into the pipette tip from the vial.

35. The vial processing system of claim 31, further comprising an ultrasonic sensor positioned to detect fluid in an uncapped vial.

36. The vial processing system of claim 31, further comprising a mixing basket adapted to receive a vial and wherein the vial handler is further positioned to transfer a vial between the input platform, staging platform and mixing basket.

37. The vial processing system of claim 36, wherein the mixing basket further comprises an eccentric drive mechanism that agitates the basket and vial to resuspend contents of the vials.

38. The vial processing system of claim 36, wherein the mixing basket is adapted to receive a plurality of vials.

39. The vial processing system of claim 31, wherein the input platform is adapted to receive a vial holding rack having a plurality of wells adapted to receive a plurality of vials.

40. The vial processing system of claim 39, further comprising two vial holding racks, wherein the wells of a first vial holding rack are adapted to receive a first set of vials and the wells of a second vial holding rack are adapted to receive a second set of vials, and wherein the wells of the first vial holding rack have a different set of dimensions from the wells of the second vial rack.

41. The vial processing system of claim 34, wherein the vial gripper comprises a belt attached to the staging platform at one end and connected to a tightening lever arm at the other end to form at least a partial loop for receiving a vial, whereby the belt tightens around a vial disposed in the loop when force is applied to the lever arm.

42. The vial processing system of claim 41, wherein the belt is wrapped around a vial from the end connected to the staging platform to the end connected to the lever arm in the same direction as the direction of cap rotation used to remove a cap from a vial.

43. The vial processing system of claim 34, wherein the cap handler comprises at least two fingers extending parallel to and substantially equidistance radially and angularly from a central axis, and a torque sensor for sensing the force of the fingers on a vial cap being engaged, whereby the cap handler is capable of engaging vial caps of variable size.

44. The vial processing system of claim 43, further comprising a rotational drive engaging the cap handler for rotation of the cap handler about its central axis, whereby the cap handler can screw and unscrew a vial cap by actuating the rotational drive.

45. The vial processing system of claim 34, wherein the tip head assembly is aligned substantially parallel to the longitudinal axis of a tip head and comprises a collar, a beveled nozzle tip and a liquid level measurement sensor, wherein the collar is slideably attached to the nozzle tip and wherein the nozzle tip is compliant in the longitudinal direction.

46. A vial processing system comprising:
- an input platform adapted to receive a vial;
- a staging platform adapted to receive a vial;
- a vial handler positioned to transfer a vial between the input platform and staging platform;
- a cap handler positioned to engage and remove a cap of a vial in the staging platform;
- a vial gripper disposed on the staging platform to restrict movement of the vial during removal of the cap; and
- a transfer pipette assembly comprising a pipette arm and tip head assembly, the tip head assembly being mounted to the pipette arm and adapted to receive a pipette tip, the pipette arm being positioned to translate the tip head assembly between an open vial and a destination area, wherein the tip head assembly is aligned substantially parallel to the longitudinal axis of a tip head and comprises a collar, a beveled nozzle tip and a liquid level measurement sensor, wherein the collar is slideably attached to the nozzle tip and wherein the nozzle tip is compliant in the longitudinal direction.

47. The vial processing system of claim 46, further comprising a vacuum generator in communication with the tip head assembly to withdraw a predetermined volume of fluid from a vial.

48. The vial processing system of claim 47, wherein the vacuum generator comprises a volumetric pump in hydraulic communication with the transfer pipette assembly.

49. The vial processing system of claim 48, further comprising a tube connecting the volumetric pump to the transfer pipette assembly, wherein a path formed by the tube, volumetric pump and pipette assembly is at least partially filled with a substantially incompressible fluid, and partially filled with a gas to create a gaseous interface between the substantially incompressible fluid and a sample volume drawn into the pipette tip from the vial.

50. The vial processing system of claim 46, further comprising an ultrasonic sensor positioned to detect fluid in an uncapped vial.

51. The vial processing system of claim 46, further comprising a mixing basket adapted to receive a vial and wherein the vial handler is further positioned to transfer a vial between the input platform, staging platform and mixing basket.

52. The vial processing system of claim 51, wherein the mixing basket further comprises an eccentric drive mechanism that agitates the basket and vial to resuspend contents of the vials.

53. The vial processing system of claim 51, wherein the mixing basket is adapted to receive a plurality of vials.

54. The vial processing system of claim 46, wherein the input platform is adapted to receive a vial holding rack having a plurality of wells adapted to receive a plurality of vials.

55. The vial processing system of claim 54, further comprising two vial holding racks, wherein the wells of a first vial holding rack are adapted to receive a first set of vials and the wells of a second vial holding rack are adapted to receive a second set of vials, and wherein the wells of the first vial holding rack have a different set of dimensions from the wells of the second vial rack.

56. The vial processing system of claim 46, wherein the vial gripper comprises a belt attached to the staging platform at one end and connected to a tightening lever arm at the other end to form at least a partial loop for receiving a vial, whereby the belt tightens around a vial disposed in the loop when force is applied to the lever arm.

57. The vial processing system of claim 56, wherein the belt is wrapped around a vial from the end connected to the staging platform to the end connected to the lever arm in the same direction as the direction of cap rotation used to remove a cap from a vial.

58. The vial processing system of claim 46, wherein,
- the staging platform further comprises a plurality of wells sized to receive a vial and disposed along the perimeter of the staging platform, and
- the vial gripper further comprises a belt disposed along the perimeter wall of each well, a lever arm attached to each belt, and an actuator arranged to communicate with the end of a lever arm, wherein,
- each belt is attached at one end to the staging platform and at the other end to a lever arm,
- each lever arm is disposed at the perimeter of each well with a free end of the lever arm disposed toward the center of the staging platform,
- the actuator is disposed at the center of the of the staging platform in selective communication with the free end of each lever arm, and
- the staging platform, wells, belts and lever arms are rotatable with respect to the actuator whereby the actuator can selectively communicate with a lever arm through rotation of the staging platform.

59. The vial processing system of claim 46, wherein the cap handler comprises at least two fingers extending parallel to and substantially equidistance radially and angularly from a central axis, and a torque sensor for sensing the force of the fingers on a vial cap being engaged, whereby the cap handler is capable of engaging vial caps of variable size.

60. The vial processing system of claim 59, further comprising a rotational drive engaging the cap handler for rotation of the cap handler about its central axis, whereby the cap handler can screw and unscrew a vial cap by actuating the rotational drive.

* * * * *